US008685382B2

(12) United States Patent
Hennink et al.

(10) Patent No.: US 8,685,382 B2
(45) Date of Patent: Apr. 1, 2014

(54) TEMPERATURE SENSITIVE POLYMERS

(75) Inventors: Wilhelmus Everhardus Hennink, Waddinxveen (NL); Cornelis Franciscus Van Nostrum, Vlijmen (NL); Marinus Jacob Van Steenbergen, Ede (NL); Osamu Soga, Ibaraki (JP); Cristianne Johanna Ferdinand Rijcken, Utrecht (NL)

(73) Assignee: Cristal Delivery B.V., Utrecht (NL)

( * ) Notice: Subject to any disclaimer, the term of this patent is extended or adjusted under 35 U.S.C. 154(b) by 0 days.

(21) Appl. No.: 13/243,926

(22) Filed: Sep. 23, 2011

(65) Prior Publication Data
US 2012/0015034 A1 Jan. 19, 2012

Related U.S. Application Data

(63) Continuation of application No. 10/593,529, filed as application No. PCT/NL2005/000203 on Mar. 17, 2005, now Pat. No. 8,110,220.

(51) Int. Cl.
*A61K 31/74* (2006.01)

(52) U.S. Cl.
USPC ....................................... 424/78.17

(58) Field of Classification Search
None
See application file for complete search history.

(56) References Cited

U.S. PATENT DOCUMENTS

| | | |
|---|---|---|
| 5,720,976 A | 2/1998 | Kim et al. |
| 5,939,453 A | 8/1999 | Heller et al. |

FOREIGN PATENT DOCUMENTS

| | | |
|---|---|---|
| EP | 0 693 508 | 1/1996 |
| WO | WO-01/09198 | 2/2001 |

OTHER PUBLICATIONS

Cadée et al., "Synthesis, characterization of 2-(methacryloyloxy)ethyl-(di-L-lactate and their application in dextran-based hydrogels," Polymer (1999) 40:6877-6881.
International Search Report for PCT/NL2005/000203, mailed on Jun. 3, 2005, 2 pages.
Neradovic et al., Thermoresponsive Polymeric Micelles with Controlled Instability Based on Hydrolytically Sensitive N-Isopropylacrylamide Copolymers, Macromolecules (2001) 34:7589-7591.
Van Dijk-Wolthuis et al., "A new class of polymerizable dextrans with hydrolysable groups: hydroxyethyl methacrylated dextran with and without oligolactate spacer," Polymer (1997) 38:6235-6242.

*Primary Examiner* — Paul Dickinson
(74) *Attorney, Agent, or Firm* — Morrison & Foerster LLP

(57) ABSTRACT

The present invention relates to compositions comprising polymers whose solubility characteristics can be changed by incubation and particularly poly (hydroxyalkyl(meth) acrylamide mono/di-lactate_interpolymers. Another aspect of this invention is the application of such temperature sensitive polymers as release systems of biologically active compounds. The polymers of the present invention comprise monomers, which have modifiable functionality. The functionality of the monomers can for example be modified by the presence of hydrolysable groups. The modification is effected by the incubation, leading to a change of the water solubility characteristics of the polymer. The polymers used in the present invention contain hydrolysable chemical groups. As a result the polymer's solution characteristics, specifically its lower critical solution temperature (LCST), change upon incubation.

23 Claims, 6 Drawing Sheets

CP (°C) of HEMAm-Lac$_2$ copolymers as a function of the mole % of HEMAm-Lac$_4$ in the copolymer.

CryoTEM picture of a 2% PEG-b-(80%HEMAm-Lac$_2$-20%HEMAm-Lac$_4$) micellar solution (bar is 200nm).

$I_{338}/I_{333}$ ratio for pyrene as a function of the concentrations of PEG-*b*- (80%HEMA-Lac$_2$-20%HEMAm-Lac$_4$).

Particle size ($Z_{ave}$) and polydispersity (PD) versus concentration of PEG-*b*-(80%HEMA-Lac$_2$-20%HEMAm-Lac$_4$) solutions.

Stability of PEG-*b*-HEMAm-Lac$_2$ versus time

Stability of PEG-*b*- (80%HEMA-Lac$_2$-20%HEMAm-Lac$_4$)

US 8,685,382 B2

TEMPERATURE SENSITIVE POLYMERS

CROSS-REFERENCE TO RELATED APPLICATION

This application is a continuation of U.S. Ser. No. 10/593,529 filed 18 Sep. 2006 which is the national phase of PCT application PCT/NL05/000203 filed 17 Mar. 2005 which claims priority from U.S. Ser. No. 10/804,302 filed 18 Mar. 2004. The contents of these applications are incorporated herein by reference in their entirety.

FIELD OF THE INVENTION

The invention relates to compositions comprising polymers whose solubility characteristics can be changed by incubation. Another aspect of this invention is the application of such temperature sensitive polymers as release systems of biologically active compounds. In yet a further aspect, the invention relates to a novel class of polymers with tuneable thermosensitivity, which polymers are biodegradable forming degradation products that are either endogenous or non-toxic in the human or animal system.

The fast developments in the field of molecular biology and biotechnology have made it possible to produce a large number of pharmaceutically interesting products in large quantities. For instance, pharmaceutically active peptides and proteins can suitably be used as drugs in the treatment of life-threatening diseases, e.g. cancer, and of several types of viral, bacterial and parasital diseases; in the treatment of e.g. diabetes; in vaccines, e.g. for prophylactic aims; for anticonception purposes, and so on and so forth. Especially the specialized biological activities of these types of drugs provide tremendous advantages over other types of pharmaceutics. Also low molecular weight pharmaceuticals, such as cytostatics, antibiotics, etc., can be produced in large amounts.

In addition, it appears that at least for certain classes of pharmaceutical proteins, such as cytokines which are presently used in e.g. cancer treatments, the therapeutic efficacy is strongly dependent on effective delivery, e.g. intra- or peritumoral. In such cases, the protein drugs should be directed to the sites where their activity is needed during a prolonged period of time.

More generally, at present a large number of low molecular weight therapeutics are becoming available which may have unfavorable biopharmaceutical characteristics (low bioavailability; low dissolution characteristics; severe side effects; etc. Therefore new solubilization systems are urgently needed.

Moreover, low molecular weight drugs, e.g. cytostatica such as paclitaxel, should be targeted towards specific sites in a body. Suitable drug targeting systems for targeted release are, e.g. micellar structures for release of low molecular weight drugs.

Hence, there is a need for delivery systems which have the capacity for sustained, controlled and/or targeted release. In the art, delivery systems comprising soluble polymers have been proposed. Such delivery systems can be obtained by using such soluble polymers for example in the form of microparticles in which the drug is encapsulated. The polymer can be present throughout each microparticle, with the drug captured within the different polymer molecules. Alternatively, the polymer forms the outer membrane of the microparticle which contains the drug. However, in vitro or in vivo application of such systems has some inherent drawbacks. First, organic solvents have to be used to encapsulate drugs in the microparticles. Second, acidic products are frequently formed during degradation, which might result in a lowering of the pH. Both a low pH and organic solvents can affect drug stability, especially if the drug is a protein. Furthermore, it appears to be difficult to control the drug release from these systems, which can lead to a burst release (see in this respect Van de Weert et al. Protein instability in poly(lactic-co-glycolic acid) microparticles, Pharm Res (2000); 17:1159-1167).

The present inventors have found that the use of temperature sensitive polymers, and especially those with a lower critical solution temperature, has a number of advantages.

Temperature sensitive (or thermosensitive) polymers with a lower critical solution temperature (LCST) are presently under investigation for biomedical and pharmaceutical applications. Thermosensitive polymers having a LCST are remarkable materials, in that below this temperature such polymers are soluble, and above it they precipitate. The lower critical solution temperature can be defined as the temperature at the point of inflection in a graph representing the amount of solids in the sample (for example as measured using light scattering techniques) vs. temperature. Alternatively, the LCST can be defined as the lowest temperature where precipitated polymer particles are detected (the 'onset' temperature). An example of a light scattering curve is shown in FIG. 1. Both the temperature at the point of inflection and the onset temperature are marked. Unless otherwise indicated, in the present description LCST is defined by the onset.

Thermosensitive polymers with LCST are soluble in aqueous solutions below the cloud point (CP), but precipitate above this temperature due to the dehydration of the polymer chains.

LCST-polymers can be used advantageously as drug release systems, because their preparation can be carried out at a temperature which is lower than the temperature at which the release is to be effected, for example the body temperature. Since the temperature can be kept low, there is little risk of denaturation or degradation of the (protein) drug to be released. Another important advantage of the use of LCST-polymers in drug release systems is that the loading of the drug delivery system can be accomplished in an aqueous system, avoiding the use of toxic organic solvents. In addition, the LCST-polymers can be chosen such that they are degradable and/or can easily be excreted by the kidneys, once in soluble form.

BACKGROUND OF THE STATE OF THE ART

The use of LCST polymers as controlled release systems is e.g. known from U.S. Pat. No. 5,720,976. In this publication release systems are disclosed, wherein an active ingredient is encapsulated in liposomes. LCST polymers are grafted to the surface of liposomes. By choosing the ratio of respective monomers in the LCST polymers, the LCST value of the polymers can be adjusted.

Furthermore, WO-A-92/07881 discloses that the solubility of polyacrylamide changes as a result of the presence of amide groups, which groups have a buffering effect. This pertains to the solubility per se, not to the LCST, which is not mentioned in this publication.

Also in EP-A-0 693 508 and in DE-A-4 023 578, it is described that the temperature sensitivity of certain polymers can be influenced by varying the ratio of the comonomers present in these certain polymers.

None of these prior art documents teach or suggest however, that LCST polymer systems can be modified, as is done in accordance with the present invention in such a way, that the LCST value of the polymers changes during incubation and as a result of incubation, and by which the above mentioned advantages of the present invention can be obtained.

In WO 01/09198, it is disclosed that a temperature sensitive polymer can be obtained by choosing a monomer that is suitable for the envisaged application, e.g. a monomer that forms a pharmaceutically acceptable polymer. Suitable monomers are the monomers selected from the group comprising ethylene glycol, lactic acid, acrylamide, methacrylamide, acrylic acid, and derivates and substituted species thereof. These monomers and/or other monomers are then reacted under suitable conditions to form homopolymers of one of these monomers or copolymers, terpolymers or other polymers of two or more monomers.

In a preferred embodiment of the invention described in WO 01/09198, the change of solubility characteristics is effected by hydrolysis of a group, such as a lactate, present on at least one of the monomers that form the polymer. In case of an in vivo application such a group can advantageously be an enzymatically or chemically hydrolyzable group. The ester groups are introduced in the polymer by choosing suitable monomers as a starting material. The monomers can be provided with ester groups by techniques known to the person skilled in the art.

In WO 01/09198 the preferred embodiment is based on poly(N-isopropylacrylamide) (PNIPAAm), which has its CP (in water) around 32° C. It is the most extensively studied thermosensitive polymer and is used for the design of thermosensitive drug delivery systems such as polymeric micelles and hydrogels. This polymer has also been used to modify the surface properties of liposomes. The CP of PNIPAAm can be modulated by copolymerising with hydrophobic or hydrophilic comonomers: hydrophobic comonomers decrease the CP whereas hydrophilic comonomers have the opposite effect.

The most preferred thermosensitive polymers of WO 01/09198 are thermosensitive copolymers of NIPAAm and N-(2-hydroxypropyl)methacrylamide lactate (poly(NIPAAm-co-HPMAm-lactate)) and their block copolymers with poly(ethylene glycol) (poly(NIPAAm-co-HPMAm-lactate)-b-PEG). When 35 mol % HPMAm-lactate was copolymerised with NIPAAm, these polymers had their CP below body temperature, whereas after hydrolysis of the lactate side chain the CP increased above 37° C. As a result, polymeric micelles formed with poly(NIPAAm-co-HPMAm-lactate)-b-PEG showed controlled instability at body temperature.

BRIEF DESCRIPTION OF THE INVENTION

The invention relates to a temperature sensitive polymer having a lower critical solution temperature that changes during incubation in an aqueous solution or medium, which polymer is a homo or interpolymer of a hydrophobically modified hydroxyalkyl(meth)acrylamide. The hydrophobical modification may in particular be effected by a hydrophobic unit, bound to the hydroxyalkyl(meth)acrylamide via a degradable bond (such as a lactate ester).

As used herein the term "hydrophobically modified" in a polymer according to the invention means that the distribution coefficient P of the hydrophobically modified polymer is lower than that of the same polymer without the modification. P can be determined by mixing an amount of the polymer in a two-phase system of equal amounts of water and octanol, letting the system phase separate, measuring the equilibrium concentrations of the polymer in the water and the octanol and divide the concentration in water by de concentration in octanol.

Preferably log P is reduced by at least 0.1. More in particular hydrophobic modification results in a reduction of the cloud point of the polymer, compared to the unmodified hydroxyalkyl(meth)acrylamide, to a cloud point of 37° C. or less. Suitable hydrophobic units include lactates, alkyl groups and aryl groups.

The alkyl may be a linear, branched or cyclic alkyl. It may have from 1 to 40 carbon atoms, in particular from 2 to 18 carbon atoms. Examples of alkyl groups include fatty acid ester residues.

Suitable aryl groups include arylgroups having from 4-40 carbon atoms, in particular from 6 to 18 carbon atoms.

The lactate may be a monolactate or an oligolactate. The term oligolactate in particular encompasses oligomers of lactic acid comprising 2-10 lactic acid residues.

The alkyl in hydroxyalkyl(meth)acrylamide is preferably selected from the group consisting of methyl, ethyl, propyl, butyl, pentyl and hexyl. These alkyls include all constitutional isomers of said alkyls (such as the n-alkyl and the isoalkyl).

A relatively small alkyl, such as methyl or ethyl is in particular considered suitable for imparting a relatively low hydrophobicity of the polymer, and/or relatively high cloud point (CP) (compared to propyl), whereas a relatively large alkyl (such as butyl, pentyl or hexyl) may have the opposite effect.

The hydroxy alkyl may be a primary hydroxyl alkyl, a secondary hydroxyl alkyl or a tertiary hydroxyl alkyl. A hydrophobically modified polymer of primary hydroxyl alkyl usually has a higher hydrolysis rate than a comparable polymer of a secondary hydroxyl alkyl, which in turn usually has a higher hydrolysis rate than a comparable polymer of a tertiary hydroxyl alkyl. Thus, depending on the desired hydrolysis rate a polymer derived from a primary, secondary respectively tertiary hydroxyl alkyl may be preferred.

Preferably, the polymer is a homo or interpolymer of a N-(2-hydroxyalkyl) (meth)acrylamide modified with a hydrophobic unit, such as a lactate, an alkyl or an aryl.

More preferably, said polymer is selected from the group consisting of homopolymers and interpolymers of (hydrophobically modified N-(2-hydroxyethyl)methacrylamide), (hydrophobically modified N-(2-hydroxyethyl)acrylamide), (hydrophobically modified N-(2-hydroxypropyl)methacrylamide) and (hydrophobically modified N-(2-hydroxypropyl) acrylamide).

In an embodiment, the polymer is hydrophobically modified by a monolactate, a dilactate, a trilactate or a tetralactate, preferably a monolactate or a dilactate of the said hydroxyalkyl(meth)acrylamides. The polymer may be a copolymer or a blend of different hydrophobically modified hydroxyalkyl (meth)acrylamide polymers.

In an embodiment the blend or copolymer is a blend respectively copolymer of at least two polymers respectively chemically bound polymer units according to the invention having a different number of lactate moieties.

The presence of a lactate polymer other than the monolactate and dilactate (i.e. the presence of trilactate, tetralactate or higher) may in particular be useful for providing a polymer (blend) with a relatively low cloud point (CP), in particular a CP below 20° C., thus providing a blend or copolymer (aggregate) with improved stability under ambient conditions. For such purpose a tetralactate polymer according to the invention is considered particularly suitable. The amount of higher lactates may be chosen within wide limits. Good results have been achieved with a copolymer, in particular a pHEMAm-dilactaat, wherein at least 5% of the monomers are other than mono- and dilactate. For good water solubility not more than 22% of the monomers are other than mono- and dilactate. Further, a polymer according to the invention with one or more lactate side chains of at least three lactic acid units (trilactate), in particular of at least four lactic acid units (tetralactate) has been found suitable to provide micelles of the polymer with improved stability, compared to the analogous polymer comprising only mono-, or dilactate units. It should be noted that this in particular holds true for polymers further comprising a hydrophilic group (e.g. PEG) as will be discussed in detail below A polymer according to the invention preferably has a lower critical solution temperature before incubation below mammalian body (i.e. core) temperature, more preferably below ambient temperature (in particular below 20° C.). In addition the lower critical solution temperature after incubation is preferably above mammalian body temperature (i.e. core temperature). In a preferred embodiment the mammalian body temperature is human body temperature, i.e. above about 37° C.

In addition, the invention relates to a blend of polymers comprising one or more polymers according to the invention. Particularly suitable blends include a blend of hydroxyethyl (meth)acrylamide lactate and at least one other hydroxyalkyl (meth)acrylamide lactate respectively a blend of hydroxypropyl (meth)acrylamide lactate and at least one other hydroxyalkyl(meth)acrylamide lactate. Preferably, the hydroxyethyl/propyl and/or alkyl moieties are N-(2-hydroxyethyl), N-(2-hydroxypropyl), respectively N-(2-hydroxyalkyl).

The invention further provides a controlled release system comprising a temperature sensitive polymer according to any one of the preceding claims and an active ingredient, such as a drug. Particularly suitable drugs include hydrophobic drugs with a low water-solubility. Such drugs include paclitaxel and other cytostatics, amphoteracin, corticosteroids, and photosensitizers.

In a preferred embodiment, the controlled release system comprises the polymer according to the invention in the form of a polymeric micelle. In such an embodiment, the polymer usually comprises a hydrophilic block which preferably comprises a polyalkyleneglycol, more preferably a poly(ethyleneglycol). The number average molecular weight of the hydrophilic block (as determined by size exclusion chromatography) is preferably in the range of about 500-10000 g/mol. The polymer capable of forming the micelle may be of the type AB, ABA or BAB (wherein A and B are respectively the hydrophilic and hydrophobic block)

In an embodiment the controlled release system is in the form of a hydrogel. In particular in such an embodiment, the polymer according to the invention is an ABA block copolymer or a BAB block copolymer, wherein block A is the temperature sensitive hydrophobically modified poly(hydroxyalkyl (meth)acrylamide) as defined herein and B is a hydrophilic polymer, preferably a polyalkyleneglycol, more preferably a poly(ethyleneglycol). The number average molecular weight of the hydrophilic block (as determined by size exclusion chromatography) is preferably in the range of about 500-10000 g/mol.

The invention further relates to a targeting drug composition, comprising a drug and particles of a controlled release system according to the invention, which particles preferably have a weight average diameter of less than 200 nm, more preferably in the range of 10 to 100 nm (as determined by dynamic light scattering)

In an embodiment, the targeting drug composition comprises a homing device.

DETAILED DESCRIPTION OF THE INVENTION

Figure 1:
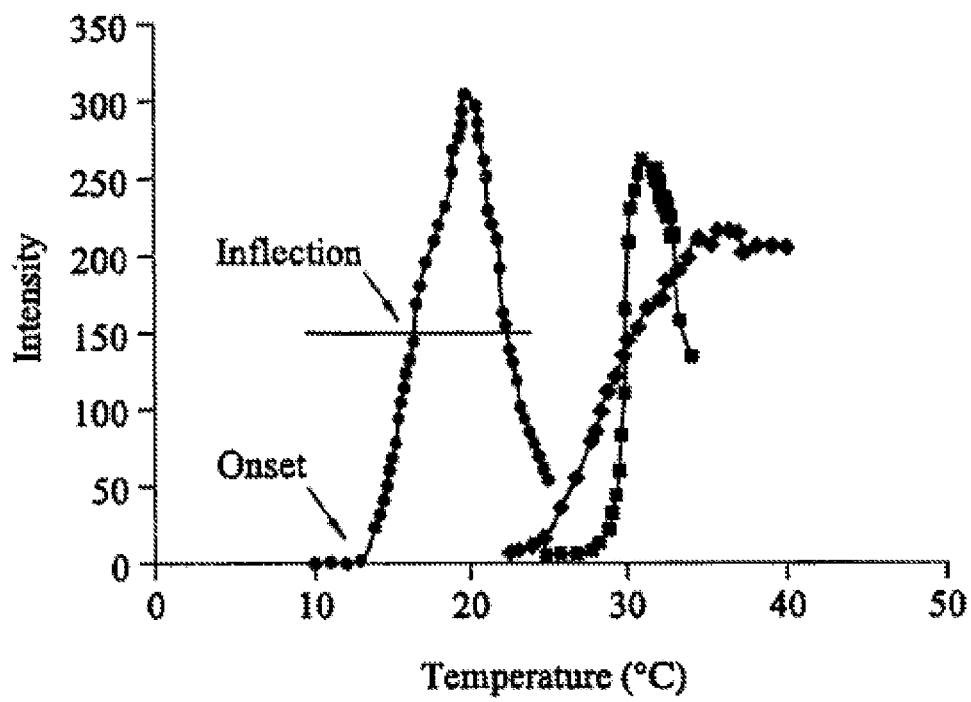
FIG. 1 shows a light scattering curve, wherein both the temperature at the point of inflection and the onset temperature are marked.

The drug delivery systems based on LCST-polymers can be prepared conveniently by introduction of the drug (such as a protein, a low molecular weight drug or another biologically active agent) into the polymer matrix. This is obtained by mixing the drug with the polymer, which is in dissolved state, for example because it is below its LCST. Subsequently, the mixture is brought in a state in which the polymer precipitates, for example by bringing it above its LCST, by which process the protein drug is captured within the precipitating polymer matrix, thus yielding a drug delivery system.

For the use in drug delivery systems, it is essential that the LCST-polymer to be applied is above its critical solubility temperature. Effective application as controlled release system can only be obtained when the in vivo temperature is above the critical solution temperature. Although it is known in the art—see e.g. the above discussed publications—that LCST-polymers can be modified by changing their composition, it will be clear that a choice with respect to the LCST has to be made prior to the administration. Once a certain polymer is chosen, its LCST is fixed. Variations of the application temperatures, as can occur easily for example as a result of differences or variations in body temperature, can lead consequently to different and non-gradual release profiles.

Said in other words, for biomedical and pharmaceutical applications of thermosensitive polymers, it is important to have possibilities to control the CP around body temperature. Furthermore, polymers of which the CP's increase from below to above body temperature in time are very attractive materials, because e.g. the controlled release of drugs without thermal treatment is feasible using such polymers.

The present invention provides a polymer that is suitable for use in a controlled release system. Consequently, this polymer can be applied as a controlled release system having all the aforementioned advantages.

The present inventors have found that when certain water soluble polymers are chemically modified, their critical solution temperature will vary in situ, viz. upon in vivo or in vitro application in an aqueous environment. These changes are time dependent. In this description and the appending claims, application in an aqueous environment, under conditions enabling the reactions that result in the change of critical temperature, for example as a result of hydrolysis, is referred to as incubation. It is also possible that the incubation is effected by enzymes present in the aqueous environment.

The polymer of the present invention comprises monomers which have modifiable functionality. The functionality of the monomers can for example be modified by the presence of hydrolysable groups. The modification is effected by the incubation, leading to a change of the water solubility characteristics of the polymer.

When reference is made to a polymer in this description, also homopolymers, copolymers, terpolymers, graft polymers, (highly) branched polymers and other interpolymers are to be understood. In fact, copolymers and terpolymers have the additional advantage that they provide an extra parameter affecting the final result, since different monomers, having different solubility characteristics, can be incorporated in one polymer, as to adjust the solubility characteristics (such as the solubility itself or the temperature dependency of the solubility) of the resulting copolymer. Copolymers and terpolymers thus form a preferred embodiment of the present invention.

The polymer according to the present invention is suitably obtained by choosing the properties of the monomers such that upon incubation the functionality of the monomers changes and as a result the solubility and/or the temperature dependency of the solubility of the entire polymer, changes.

In a particular embodiment, the monomers are chosen so that their hydrophilicity changes upon incubation. As a result, the hydrophilicity of the entire polymer will change upon incubation. This will lead to a polymer with a different solubility and/or temperature dependency of the solubility.

As indicated above, poly(NIPAAm-co-HPMAm-lactate)-b-PEGm, as described in WO 01/09198 may show controlled instability at body temperature. Upon further investigation, the present inventors have realised that the biodegradability of PNIPAAm should be improved. Moreover, the biocompatibility and possible toxic-side effects of PNIPAAm are not well-known at present. In their investigations, the present inventors have found that a favorable system can be based on HPMAm and/or other hydroxyalkyl(meth)acrylamide based polymers that are hydrophobically modified by a hydrolysable group.

The hydrolysable group may for instance be bound by a bond selected from esters, orthoesters, amides, carbonates, carbamates, anhydrides, ketals, and acetals, preferably by an ester bond.

The present invention therefore in particular relates to a novel class of such thermosensitive and biodegradable polymers which may be described as poly(hydroxyalkyl(meth) acrylamide lactate), wherein the number of lactates per hydroxyalkyl(meth)acrylamide is generally 1, 2, 3, 4, 5, 6, 7, 8, 9 or 10. Such a polymer may be represented by the following formula of the monomeric units constituting the polymer:

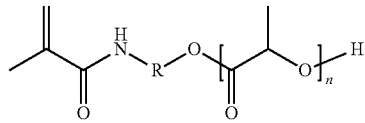

wherein R is the alkyl (which may be linear or branched) and n the number of lactate moieties. The ester moiety may be coupled to the R at any position of the alkyl chain, Thus the position of the ester relative to the amide may be $\alpha, \beta, \gamma, \delta, \in$ (etc), or $\omega$ position.

Particular suitable examples of polymers according to the invention are (homo)polymers of a (N-2-hydroxypropyl) methacrylamide lactate, (N-2-hydroxyethyl)methacrylamide lactate, (N-hydroxymethyl)methacrylamide lactate, (N-2-hydroxybutyl)methacrylamide lactate, (N-2-hydroxypentyl) methacrylamide lactate or (N-2-hydroxyhexyl)methacrylamide lactate.

Especially favoured are poly(N-(2-hydroxypropyl)methacrylamide mono/di lactate) (poly(HPMAm-mono/di lactate)), poly(N-(2-hydroxyethyl)methacrylamide mono/di lactate) (poly(HEMAm-mono/di lactate)), poly(N-(hydroxymethyl)methacrylamide mono/di lactate) (poly(HMMAm-mono/di lactate)), poly(N-(2-hydroxybutyl)methacrylamide mono/di lactate) (poly(HBMAm-mono/di lactate)), poly(N-(2-hydroxypentyl)methacrylamide mono/di lactate) (poly(HPeMAm-mono/di lactate)) respectively poly(N-(2-hydroxyhexyl)methacrylamide mono/di lactate) (poly(HHMAm-mono/di lactate)).

In the present description and the appending claims, the term "interpolymer" refers to a polymer comprising at least two types of monomers, and hence encompasses copolymers, terpolymers, etc.

Preferably, the invention relates to homopolymers of HPMAm-dilactate, HEMAm-dilactate and other hydrophilic monomers such as HEMAm-monolactate, HPMAm-monolactate, HEMAm-(lactate)$_n$, HPMAm-(lactate)$_n$, wherein n is an integer from 3 to 10, in particular from 3 to 5; HPMAm; or hydroxy(C$_{1-6}$ alkyl)methacrylate. Also terpolymers of poly (hydroxyalkyl (meth)acrylamide-mono/dilactate), such as poly(HPMAm-mono/dilactate) or poly(HEMAm-mono/dilactate), and a further hydrophilic monomer are suitable to be used.

The cloud points (CP) of a poly(HPMAm-monolactate) and poly(HPMAm-dilactate) in water were 65° C. and 13° C., respectively. The lower CP for poly(HPMAm-dilactate) is likely due the greater hydrophobicity of the dilactate side group over the monolactate side group. The CP of poly(HPMAm-monolactate-co-HPMAm-dilactate) increased linearly with the mole percentage of HPMA-monolactate, which demonstrates that the CP is tuneable by the copolymer composition. Likewise, the CP of poly(HEMAm-dilacate-co-HEMAm-tetralactate) decreased linearly with the mole percentage of the more hydrophobic HEMAm-tetralactate.

Hence, in an aspect, the present invention relates to a temperature sensitive polymer having a lower critical solution temperature that changes during incubation in an aqueous solution or medium, which polymer is a homo- or interpolymer of a (N-(hydroxyalkyl)methacrylamide lactate). In a preferred embodiment said N-(hydroxyalkyl)methacrylamide lactate is the mono- or dilactate, more preferably the dilactate. The alkyl is preferably propyl or ethyl.

The term "mono/dilactate" means that part of the monomers used in the polymers of the invention are in the monolactate form, and part or all of the monomers used in the polymers of the invention are in the dilactate form.

Due to the hydrolysable lactic acid side groups the CP will increase in time with lactic acid, an endogenous compound, and the water-soluble poly(hydroxyalkyl(meth)acrylamide) (such as pHPMAm, pHEMAm) as degradation products. In particular, pHPMAm is a well-known non-toxic macromolecular carrier which is, among others, used for the development of polymeric prodrugs of cytostatic agents. A good biocompatibility of a polymer according to the invention is expected, in particular for poly(HPMAm-lactate), especially because pHPMAm systems have recently entered into clinical trials.

The polymer can be synthesized by starting from a mixture of the monomers and carrying out the polymerization reaction. It is also possible to first produce the polymer and subsequently functionalize it by coupling suitable groups. Compositions according to the present invention comprise block copolymers or terpolymers, random copolymers or terpolymers, random copolymers and polymeric networks, all of which polymers can be grafted, and mixtures (blends) thereof.

The solubility characteristics of the compositions according to the present invention will change upon incubation, for example when contacted with aqueous media, such as will be the case in in vivo application.

For application in mammals, the polymers according to the present invention have a critical temperature for the composition as synthesized which is below body temperature and preferably below ambient temperature, viz. between about 0 to 36° C., preferably between 0 and 20° C., and most preferably between 5 and 10° C. However, more preferably the value of LCST crosses the normal human body temperature (which is typically 37° C.) upon incubation so that the LCST before incubation is below 37° C., preferably below 20° C., and LCST after incubation is above 37° C., preferably above 38° C.

A preferred embodiment of the present invention is the use of the temperature sensitive polymer in or as a controlled release system which further comprises an active ingredient. Such systems are for example suitable for the controlled administration of drugs, such as protein drugs.

The controlled release system of the present invention can be used for the release of biologically active compounds, such as pharmaceutic compounds, e.g. pharmaceutically active peptides and proteins, genetic material e.g. nucleotides, RNA and DNA, plasmid DNA, anti-sense oligonucleotides, si-RNA, nutrients, low molecular drugs, imaging agents, etc. As mentioned above, hydrogels are especially suitable for the release of proteins and similar compounds, whereas micellar systems are suitable as carriers for low molecular weight drugs.

When the system is used for the delivery of genetic material, e.g. the delivery of plasmid DNA, anti-sense oligonucleotides or si-RNA, the LCST polymer of the invention preferably comprises cationic groups, such as DMAEMA (=dimethyl amino ethyl methacrylate).

It is also possible to make the controlled release systems which can be obtained by the present invention in the form of polymeric micelles. Polymeric micelles can be formed by the synthesis of amphiphilic blockcopolymers, e.g. AB block copolymers of a polyalkylene glycol, such as PEG, and a hydrophobic or thermosensitive block. In aqueous solutions, these polymers form micelles with a size of around 20-100 nm similar to those of the method of G. S. Kwon, et al. Langmuir, 9 (1993), 945-949). The hydrophobic core of these micelles can be loaded with drugs, e.g. an anti-cancer agent, such as adriamycin or paclitaxel). After in vivo administration of these systems the adriamycin loaded micelles selectively accumulate in certain tumors, simultaneously releasing the drug, which results in killing of tumor cells (cfr. M. Yokoyama, et al. Journal of Controlled Release, 50 (1998) 79-92).

Polymers with an LCST have also been applied to design polymeric micelles. Below the LCST, the thermosensitive polymer acts as hydrophilic part of the system (e.g. in AB blockcopolymers of NIPAA and styrene; cfr. S. Cammas, et al. Journal of Controlled Release, 48 (1997) 157-164).

Also, systems have been described in which PNIPAA forms the hydrophobic part of the polymeric micelle (in block copolymers of poly(ethylene glycol) and poly(N-isopropylacrylamide); M. D. C. Topp, et al. Macromolecules, 30 (1997) 8518-8520). After administration of these drug loaded PNIPAA systems and arrival at the target site, drug release can then be triggered by local hypothermia. Hypothermia is, however, not easily done or technically feasible for all tissues and organs, which limits the applicability of these systems.

These disadvantages can be overcome by using polymers composed of a hydrophilic block covalently linked to a block composed of thermosensitive polymer with hydrolyzable side groups. Such a hydrophilic block preferably comprises a polyalkylene glycol, in particular a poly(ethyleneglycol) (PEG). When the LCST of the thermosensitive block is initially below body temperature, polymeric micelles are formed at 37° C. Due to hydrolysis of the side groups present in the thermosensitive block of the system, the LCST will increase, resulting in destabilization of the micelle when the LCST passes 37° C. When a drug is incorporated in the hydrophobic core, its release will be affected by this process. These systems can be favorably applied in e.g. cancer treatment, treatment of rheumatism, arthritis, infections and/or other inflammations.

As mentioned above, the polymers of the present invention comprise all possible polymer architectures, such as (multi-) block copolymers (such as AB, ABA, ABAB, etc.) or graft copolymers, random copolymers or terpolymers, or polymeric networks; all of which may be grafted.

AB blockcopolymers with a thermosensitive block A (i.e. the block of the hydrophobically modified hydroxyalkyl (meth)acrylamide) polymer of the invention) and a water-soluble B block (e.g. PEG or pHPMAm) that form micelles when the LCST is passed, can be obtained by any known technique in the art for making AB blockcopolymers. Conveniently, these polymers are prepared using a so called macroinitiator.

A macroinitiator is a macromolecular initiator that is formed e.g. by coupling a low molecular weight initiator, such as 4,4'-azobis(4-cyanopentanoic acid), (HO—CO—CH$_2$—CH$_2$—C(CH$_3$)(CN)—N=)$_2$ (ABCPA), via its carboxyl groups at to the terminal OH group of a compound such as methoxylated PEG (i.e. CH$_3$—O-PEG-OH). In this way a compound of the formula (CH$_3$—O-PEG)$_2$-ABCPA is formed. Typically, PEG with a Mw of about 500-10000 g/mol, in particular of about 1500-10000 g/mol, is used for this purpose. Preferably PEG with a Mw of about 5000 g/mol (PEG 5000) is used to form a (PEG 5000)-2-ABCPA macroinitiator. When this initiator decomposes by heat, a PEG chain with one radical is formed. This radical subsequently initiates the polymerization of monomers (such as HPMAm-mono- and dilactate, as described hereinbelow), by which an AB block copolymer is formed. In aqueous solution such polymers form a micellar structure when the temperature rises above its LCST. These micelles destabilize when the hydrolysis results in an A block with an increased LCST (above the temperature at which the micelles are applied, preferably at body temperature). Alternatively, the block copolymers can be prepared by controlled radical polymerization techniques such as atom transfer radical polymerization (ATRP) or reversible addition-fragmentation chain transfer (RAFT) polymerization using macroinitiators, macro-RAFT-agents, or sequential monomer addition.

ABA block copolymers may be synthesized via any of the above mentioned techniques, e.g. the macroinitiator route by using instead of a monofunctional (i.e. α-methoxy) PEG or equivalent thereof, an α-ω-hydroxyl derived macroinitiator, viz. a polyester macroinitiator which has the ABCPA-groups alternating with PEG groups. When this initiator decomposes by heat, PEG chains with two radicals are formed. These radicals subsequently initiate the polymerization of monomers (such as HPMAm-mono- and dilactate), by which an ABA block copolymer is formed. The ABA block copolymers formed by this route will be soluble in water below the LCST. When the temperature is risen above the LCST of block A, a phase separated system will be formed, wherein as a result of the choice of block copolymer architecture, a hydrogel will be obtained. This hydrogel will dissolve gradually when the LCST of block A increases to above 37° C., due to the hydrolysis of the groups present on the monomers of this block. These systems are especially suitable for immobilizing cells, which can be employed in biotechnology and tissue engineering. Like the other systems mentioned hereinabove, these hydrogel systems can also be used as matrix for controlled release of active ingredients, in particular pharmaceutical proteins.

It is noted, however, that also the ABA block copolymers—like the AB block copolymers—may also be prepared by other, conventional synthesis routes, as indicated above (e.g. by RAFT polymerization).

In Examples 3 and 4 herein-below, the synthesis of AB and ABA block copolymers are illustrated.

The controlled release system of the present invention may be in the form of a hydrogel. The hydrogel may comprise an ABA block copolymer wherein block A is a temperature sensitive polymer according to the invention and B is a hydrophilic polymer and preferably it is PEG. Such ABA block copolymers and hydrogels have the advantages described above.

When the polymers of the present invention are used for targeting drug purposes, the release system is made of particles, which particles have an average diameter of less than 1 μm, preferably less than 100 nm. To be of practical value, these particles will usually have to be larger than several nm, e.g. greater than 10 nm as determined by light scattering.

The ratio of different monomers, and especially the mono/dilactate ratio which constitute the interpolymer of the invention, will influence the LCST and its development upon incubation. Generally for practical application, e.g. application in mammals, it is desirable to choose the ratios such that the LCST before incubation is below body temperature and after incubation above body temperature. The optimal ratio of each of the monomers will consequently depend strongly on the materials used and the envisaged application. The optimal values can be determined experimentally, as will be illustrated in the Examples hereinafter.

An important aspect of the present invention is the use of hydrolysable chemical groups in a temperature sensitive polymer in order to change said polymer's solution characteristics, specifically its critical solution temperature, more specifically its lower critical solution temperature (LCST).

It will be understood that apart from changing the solubility of polymers having a lower critical solution temperature, this can also be applied to polymers having a higher critical solution temperature, viz. polymers which dissolve at temperatures higher than their critical temperature, and precipitate at temperatures lower than this critical temperature.

The effect of the incubation can be an increase as well as a decrease of the critical temperature upon incubation.

The controlled release systems of the present invention can be prepared by the synthesis of a water soluble polymer. This is e.g. done by a) functionalizing a monomer with hydrolysable groups, b) optionally mixing of said monomer with at least one monomer of a different type in a suitable ratio using a suitable solvent in the presence of an initiator and/or a catalyst to form said polymer c) removing said solvent and dissolving the polymer, and d) optionally purify said polymer, such as by precipitation; in which process the functionalizing of the monomers of step a) is optionally carried out after step b) on the monomers as they are present in the polymer; and subsequently mixing said water soluble polymer with a releasable compound.

Suitable initiators and catalysts are known in the art. An example of a suitable initiator for step b) is α,α'-azoisobutyronitrile (AIBN). An example of a suitable catalyst for step a), (e.g. the grafting of HPMAm, HEMam or the like with lactide), is stannous octoate ($SnOct_2$).

The polymer of the present invention comprises one or more hydrophobically modified hydroxyalkyl methacrylamide monomers. In particular the monomers may be selected from monolactate, dilactate or higher lactate esters of the said monomers. With respect to the higher lactate, this is usually chosen in the range of 3 (trilactate) to 10 (decalactate). The hydroxyalkyl methacrylamide (such as HPMAm, HEMAm etc.) can be synthesized based upon the technology as described by D. Oupicky et al. (DNA complexes with block and graft polymers of N-2-hydroxypropyl)methacrylamide and 2-(trimethylammonio)ethyl methacrylate. J. Biomater. Sci. Polymer Ed., Vol. 10, No. 5, pp. 573-590 (1999).

The hydroxyalkyl methacrylamide (such as HPMAm, HEMAm etc.) can subsequently be esterified to mono, dilactate and higher lactate with lactide based upon the methodology as described by Neradovic. D, et al. (Degradation mechanism and kinetics of thermosensitive polyacrylamides containing lactic acid side chains. Macromolecules 36, 7491-7498, (2003)).

In principle, other monomers can be present as well. All monomers that copolymerize with the hydrophobically modified hydroxyalkyl methacrylamide (such as HPMAm-lactate, HEMAm-lactate etc) are suitable. Examples of these are acrylates, methacrylates, acrylamides, methacrylamides, N-vinyl-pyrrolidone, vinyllactates, vinylethers, etc. The amount of these comonomers that can be present will vary upon the specific monomers in question and is from 0-70 mole %, preferably from 1-50 mole %. The critical issue is the LCST behaviour, which should be maintained.

A specific polymerization reaction giving the polymers of the invention is described hereinbelow in Example 1.

Apart from application as a controlled release agent, the polymers of the present invention can be applied as release systems for a variety of compounds in different applications, such as enzymes, colorants or other additives in laundry applications, adhesives in glues, insecticides or nutrients in agricultural applications, etc. Also possible is the use for the entrapment of living cells for e.g. tissue engineering (see, in this respect, Lee K. Y. Mooney, D. J. Hydrogels for tissue engineering, Chemical Reviews 2001: 101, 1869-1879) Further possible applications are the topical administration polymers of the present invention loaded with active ingredients, e.g. for the treatment of burn wounds and ulcers. The polymers of the invention can also be used for the delivery of genetic material (DNA delivery).

The present invention will now be illustrated in the following Examples, which illustrate the invention and are not limiting the invention.

EXAMPLE 1

Figure 2:
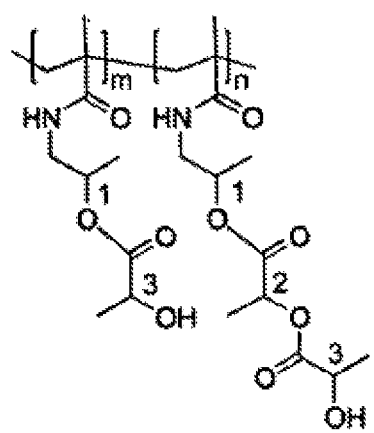
FIG. 2 gives the structure of poly(HPMAm-monolactate) (n=0), poly(HPMAm-dilactate) (m=0) and poly(HPMAm-monolactate-co-HPMAm-dilactate) (m, n≠0).

Synthesis of Poly(HPMAm-Monolactate), Poly(HPMAm-Dilactate) and their Copolymers HPMAm-monolactate and HPMAm-dilactate (synthesized as described by Neradovic et al, Thermoresponsive polymeric micelles with controlled instability based on hydrolytically sensitive N-isopropylacrylamide copolymers. Macromolecules 34, 7589-7591, 2001) were dissolved at a concentration of 0.1 g/mL in 1,4-dioxane. The HPMAm-monolactate/HPMAm-dilactate ratios were 100/0, 75/25, 50/50, 25/75, 0/100 (mol/mol). α,α'-Azoisobutyronitrile (AIBN) (total amount of monomers/AIBN is around 40/1 (mol/mol)) was added as radical initiator and the polymerization was conducted at 70° C. for 24 h in a nitrogen atmosphere. The polymers were collected by centrifugation after precipitation in diethyl ether. The polymers were further purified by dissolving them in cold water, followed by filtration through a 0.22 μm filter. After freeze-drying, the products were characterized by $^1$H NMR (solvent: CDCl$_3$) and gel permeation chromatography (GPC). GPC was done using Plgel 3 μm MIXED-D+Plgel 3 μm MIXED-E columns (Polymer Laboratories) and poly(ethylene glycol) standards. The eluent was DMF containing 10 mM LiCl, the elution rate was 0.7 mL/min. and the temperature was 40° C. The copolymer composition of the polymers was determined by $^1$H NMR from the ratio of the integral of the peak at 5.0 ppm ($I_{5.0}$, methine protons 1 and 2, FIG. 2) to the integral of the peak at 4.3 ppm ($I_{4.3}$, methine protons 3, FIG. 2) by the following formula: $I_{5.0}/I_{4.3}=1+x$, where x represents the molar fraction of HPMAm-dilactate in the copolymer.

The CP of the polymers was determined with static light scattering (SLS) using a Horiba Fluorolog® fluorometer (650 nm, at a 90° angle). The polymers were dissolved in water or in isotonic 120 mM ammonium acetate buffer (pH=5.0) at 0° C. The polymer concentration was varied between 0.1 mg/mL and 5 mg/mL. The scattering intensity was measured every 0.2° C. during heating and cooling (the heating/cooling rate was approximately 1° C./min). Onsets on the X-axis, obtained by extrapolation of the intensity-temperature curves during heating to intensity zero were considered as the CP. The CP determinations were done at least two times and the deviations were smaller than 0.5° C.

The results of the Example are discussed herein-below. Poly(HPMAm-monolactate), poly(HPMAm-dilactate) as well as their copolymers (FIG. 2) were synthesized by radical polymerization. Five polymers with different monomer compositions were obtained in a yield between 50 and 70% (see Table 1).

TABLE 1

Characteristics of the polymers prepared in Example 1

| | Feed ratio (mol/mol) | Ratio in polymer[a] (mol/mol) | $M_n$[b] | $M_w$[b] | $M_w/M_n$ | CP (° C.)[c] | CP (° C.)[d] |
|---|---|---|---|---|---|---|---|
| poly(HPMAm-monolactate) | 100/0 | — | 11400 | 24400 | 2.14 | 65.0 | 63.0 |
| poly(HPMAm-monolactate-co-HPMAm-dilactate) | 75/25 | 75/25 | 7500 | 17600 | 2.35 | 50.5 | 47.5 |
| | 50/50 | 51/49 | 8100 | 16900 | 2.08 | 36.5 | 34.0 |
| | 25/75 | 26/74 | 6800 | 14000 | 2.06 | 25.0 | 23.0 |
| poly(HPMAm-dilactate) | 0/100 | — | 6300 | 10700 | 1.70 | 13.0 | 10.5 |

[a]Determined by $^1$H NMR.
[b]$M_n$ = number average molar weight; $M_w$ = weight average molar weight determined by GPC
[c]Determined by SLS for 1 mg/mL solution in water.
[d]Determined by SLS for 1 mg/mL solution in isotonic 120 mM ammonium acetate buffer (pH = 5.0).

Figure 3:
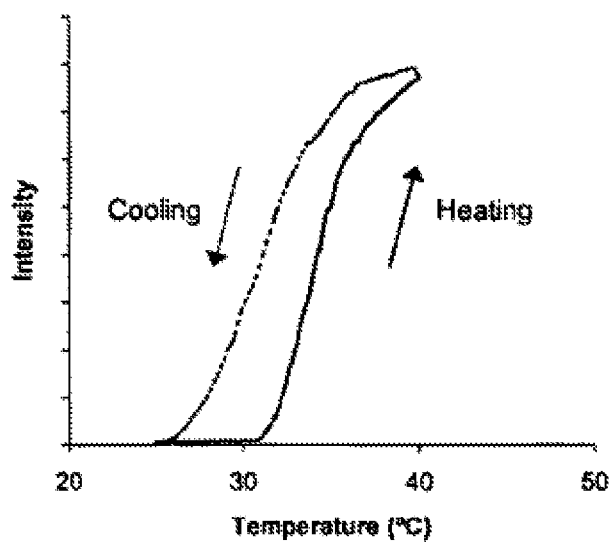
FIG. 3 shows a light scattering intensity temperature curve for poly(HPMAm-monolactate-co-HPMAm-dilactate) in isotonic 120 mM ammonium acetate buffer (pH=5.0) at 5 mg/ml. The molar ratio of HPMAm-monolactate to HPMAm-dilactate is 51:49 (mol/mol).
Figure 4:
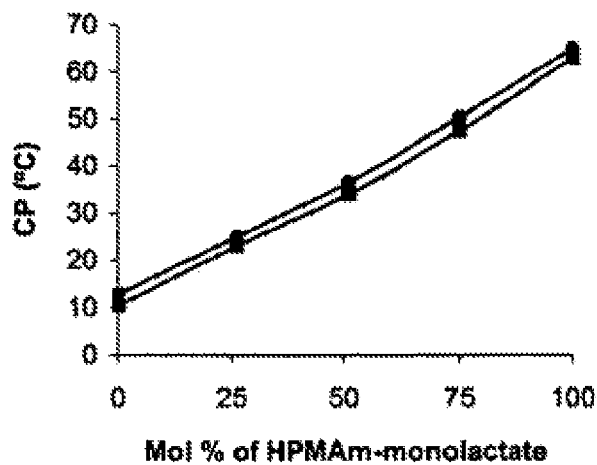
FIG. 4 shows the Cloud Point (CP) of poly(HPMAm-monolactate-co-HPMAm-dilactate) as a function of the mole-% HPMAm-monolactate in the copolymer. ● is 1 mg/mL solution in water; ■ is 1 mg/mL solution in isotonic 120 mM ammonium acetate buffer (pH=5.0).

For the copolymers, the composition was close to the feed ratio of the monomers. Static light scattering measurements of these polymers in water and in isotonic 120 mM ammonium acetate buffer (pH=5.0, to minimize hydrolysis of lactate ester side group) were performed. Interestingly, all polymers of Table 1 showed LCST behaviour. FIG. 3 shows a typical light scattering intensity-temperature curve for poly(HPMAm-monolactate-co-HPMAm-dilactate) in isotonic 120 mM ammonium acetate buffer (pH=5.0). Poly(HPMAm-monolactate) has a rather high CP (65° C. in water, Table 1) whereas poly(HPMAm-dilactate) has a relatively low CP (13° C. in water, Table 1). This can be explained by the greater hydrophobicity of the dilactate side group over the monolactate side group. Importantly, the CP of the copolymers linearly increased with mol % of HPMA-monolactate monomer (FIG. 4), meaning that the CP of the copolymers can be tailored by the copolymer composition.

Although molecular weight of the polymers decreased as the ratio of HPMAm-dilactate increased (Table 1), the decrease of molecular weight is not the reason for the decrease of the CP. Poly(HPMAm-monolactate) with lower molecular weight was prepared and it was observed that the CP slightly increased with the decrease of molecular weight.

The CP's in isotonic 120 mM ammonium acetate buffer (pH=5.0) were approximately 2.5° C. lower than those in water (Table 1). This can be attributed to a salting-out effect of ions present in the buffer solution. FIG. 3 shows that thermohysteresis of around 5° C. is observed between the heating and cooling curve. It has been reported that PNIPAAm does not show LCST hysteresis. In contrast, poly(N-isopropylmethacrylamide) shows hysteresis, which is ascribed to the α-methyl group in the polymer backbone resulting in a decreased chain flexibility.

Since the polymers of Table 1 also contain α-methyl groups in the polymer backbone, the hysteresis is likely due to the same phenomenon.

Figure 5:
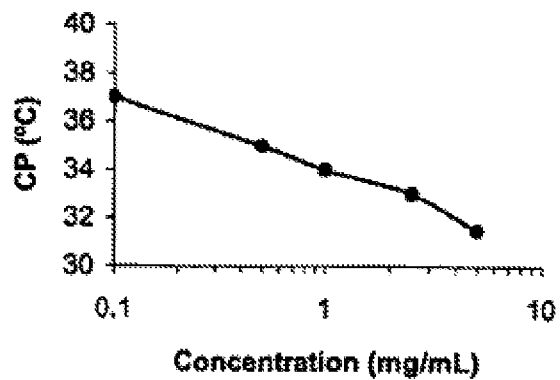
FIG. 5 shows the CP of poly(HPMAm-monolactate-co-HPMAm-dilactate 51/49) in isotonic 120 mM ammonium acetate buffer (pH=5.0) as a function of the polymer concentration.
Figure 6:
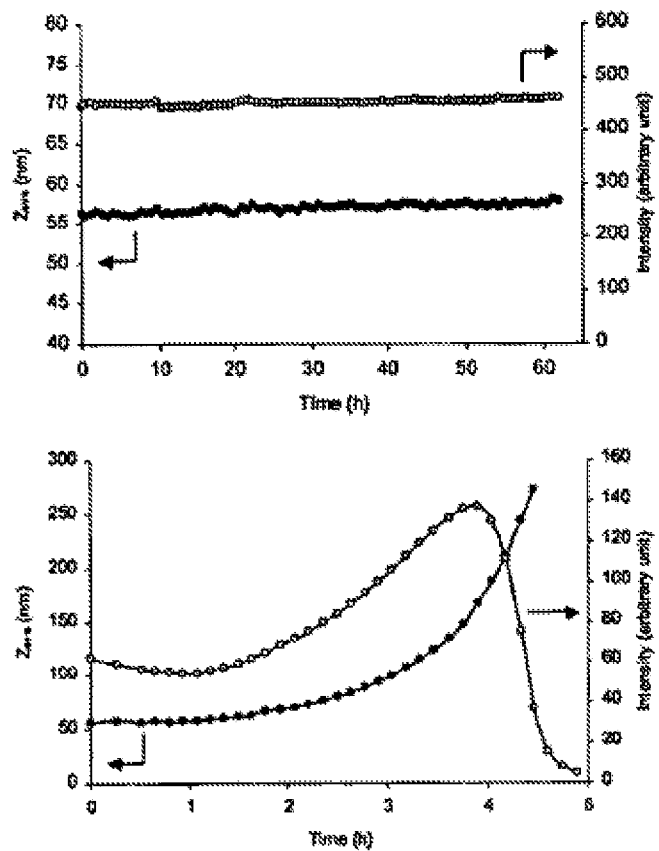
FIG. 6 shows stability data on poly(HPMAm-dilactate)-b-PEG ($M_n$-'s respectively 13600/5000) micelles at 37° C. and at pH=5.0 (top) and pH=9.0 (bottom).

FIG. 5 shows the effect of the concentration of polymer on the CP. The CP decreased approximately 3° C. as the concentration increased 10-fold. The CP of PNIPAAm is hardly affected by its concentration, while other thermosensitive polymers also show an increase of CP with a decrease in concentration.

The thermosensitive and biodegradable polymers of the invention have attractive features especially as materials for drug delivery and biomedical applications. First, the CP of the polymer can be tailored from 10° C. to 65° C. by the copolymer composition. Second, the lactic acid side groups are removed by hydrolysis in time. This means that the polymer becomes more hydrophilic in time, which is associated with an increase in CP. Therefore, polymers can be designed which are initially in their precipitated form but which become soluble in time. Further, it is expected that the polymers possess a good biocompatibility.

EXAMPLE 2

Paclitaxel Loading into Peg-b-p(HPMAm-Dilactate)

In this example the loading of Paclitaxel (PTX) into the micelles of PEG5000-b-p(HPMAm-dilactate) 13600 block copolymers was studied. Preparation of the block copolymers is described in example 3 below.

First, the polymer was dissolved at a concentration of 10 mg in 1 ml isotonic 120 mM ammonium acetate buffer with a pH of 5.0. The temperature was maintained at 0° C. by ice-cooling.

1.8 ml of this polymer solution or of the buffer as a reference was cooled with ice. Next a 0.2 ml PTX solution in ethanol was added meanwhile stirring and ice cooling the solution. To sample A and sample B 10 mg/ml PTX solution was added and to sample C 20 mg/ml. The volume ratio of PTX solution and polymer solution is 1:9. Thus 10% ethanol (v/v) is present in the mixture.

Immediately after mixing the drug and polymer solutions, the mixture was put into a water bath of 50° C. for 1 minute to form micelles. Next the solution was left at room temperature for 1 minute and subsequently filtrated with a 0.45 μm filter to remove precipitated PTX.

The DLS of the filtrate was measured at 25° C. and the amount of PTX by HPLC. The results are in Table 2 below.

TABLE 2

| | Sample | | |
|---|---|---|---|
| | A) PTX + buffer | B) PTX 1 mg/mL | C) PTX 2 mg/mL |
| PTX added (μg/mL) | 1000 | 1000 | 2000 |
| Polymer (mg/mL) | 9 | 9 | 9 |
| % Ethanol in formulation | 10 | 10 | 10 |
| Outlook after forming micelles | lots of precipitates | opalescent | opalescent |
| PTX loaded (μg/mL) | 1.4 | 1003 | 1847 |
| Loading efficiency (%) | | 100.3% | 92.4% |
| $Z_{ave}$ (PD) at 25° C. | — | 59 nm (0.059) | 66 nm (0.088) |

From Table 2 it is clear that the amount of loaded PTX increases dramatically and almost linearly with the amount of polymer used. Furthermore, it is indicated that the average particle size Z is well below 100 nm; for sample B 59 nm and for sample C 66 nm, respectively.

EXAMPLE 3

Synthesis of AB Blockcopolymers of p(HPMAm-Dilactate) (A-Block) and PEG (B-Block) (p(HPMAm-Dilactate)-b-PEG Block Copolymers (pHPMAmDL-b-PEG))

p(HPMAm-dilactate)-b-PEG block copolymers (pHPMAmDL-b-PEG) were synthesized by radical polymerisation using HPMAm-dilactate as monomer and $PEG_2$-ABCPA as macroinitiator essentially as described previously for the synthesis of block-copolymers of PEG 5000 and NIPAAm or NIPAAm-HPMAm(-lactate) (Neradovic D, Van Nostrum C F, and Hennink W E. Thermoresponsive polymeric micelles with controlled instability based on hydrolytically sensitive N-isopropylacrylamide copolymers. Macromolecules 34, 7589-7591, 2001) and schematically shown in scheme 1.

Scheme 1. Synthesis route and structure of pHPMAmDL-b-PEG block copolymer.

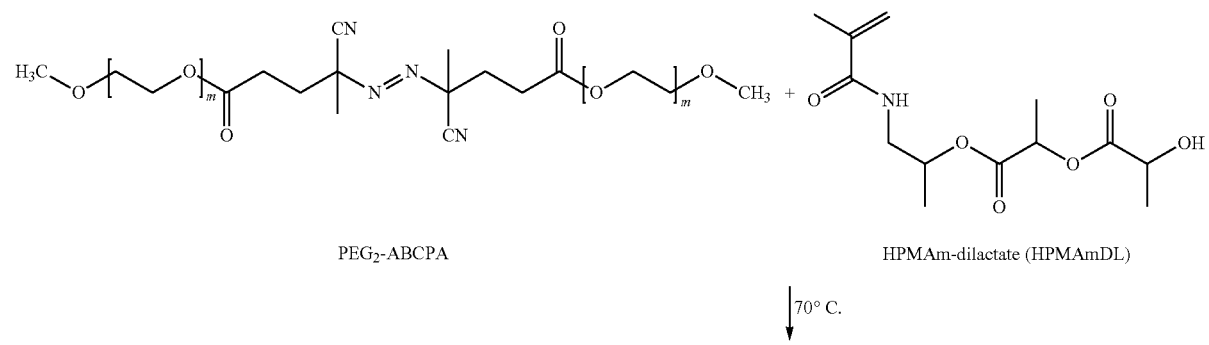

$PEG_2$-ABCPA                HPMAm-dilactate (HPMAmDL)

↓70° C.

-continued

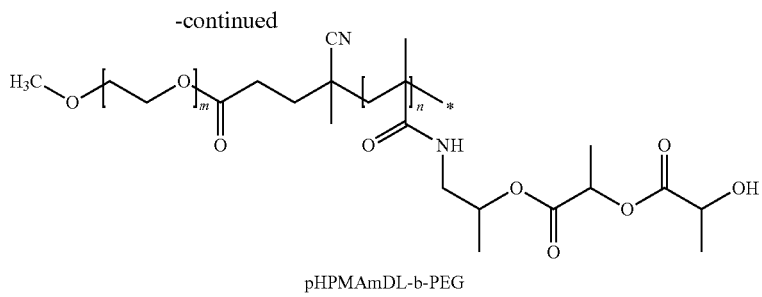

pHPMAmDL-b-PEG

The macroinitiator (PEG 5000)$_2$-ABCPA was synthesized as follows. A 50 mL round bottom flask was loaded with 2 g (0.4 mmol) polyethylene glycol 5000 monomethylether (PEG 5000), 0.056 g (0.2 mmol) 4,4-azobis(4-cyanopentanoic acid) (ABCPA), 0.0189 g (0.06 mmol) 4-(dimethylamino)-pyridinium-4-toluene-sulfonate (DPTS) and 0.125 g (0.6 mmol) N,N'-dicyclohexylcarbodiimide (DCC). The flask was evacuated and filled with nitrogen. Next, 3 mL of 1:1 mixture of dichloromethane (stabilized with amylene) and dry DMF was added using a syringe. The mixture was stirred at room temperature for 24 hours. Next, the reaction mixture was filtered, the solid was washed with dichloromethane and the combined organic solutions were evaporated.

Thereafter, the product was dissolved in toluene, remaining insoluble substances were removed by filtration, and the solvent was evaporated. The obtained dry product was extracted with diethyl ether to remove traces of dicyclohexyl urea (DCU). The product obtained was dissolved in water and the solution was filtered to remove remaining solid. The product was collected after freeze-drying (yield 80%). This macroinitiator is used for the synthesis of p(HPMAm-dilactate)-b-PEG block copolymers (pHPMAmDL-b-PEG). In detail: HPMAm-dilactate and PEG$_2$-ABCPA were dissolved at a total concentration of 0.3 g/mL in acetonitrile. To obtain block copolymers with different pHPMAmDL block lengths, the ratio of monomer to macroinitiator was varied between 35/1 to 140/1 (mol/mol).

The polymerization was conducted at 70° C. for 24 hours in a nitrogen atmosphere. The polymers were collected by centrifugation after precipitation in diethyl ether. The polymers were further purified by dissolving these in cold water, followed by filtration through a 0.22 μm filter and freeze-drying. The products were characterized by $^1$H NMR (solvent: CDCl$_3$) with a Gemini 300 MHz spectrometer (Varian Associates Inc. NMR Instruments, Palo Alto, Calif.) and gel permeation chromatography (GPC). GPC was carried out using Plgel 3 μm MIXED-D+Plgel 3 μm MIXED-E columns (Polymer Laboratories) and poly(ethylene glycol) standards. The eluent was DMF containing 10 mM LiCl; the elution rate was 0.7 mL/min; and the temperature was 40° C.

$^1$H NMR (solvent: CDCl$_3$) (all protons are from pHPMAmDL block except for methylene protons from PEG.): δ=6.5 (b, CO—NH—CH$_2$), 5.0 (b, NH—CH$_2$—C$\underline{H}$(CH$_3$)—O and CO—C$\underline{H}$(CH$_3$)—O), 4.4 (b, CO—C H(CH$_3$)—OH), 3.6 (b, PEG methylene protons, O—CH$_2$—C $\underline{H}_2$), 3.4 (b, NH—CH$_2$—CH(CH$_3$)), 2.0-0.6 (the rest of the protons from pHPMAmDL block).

The number average molecular weight (M$_n$) of pHPMAmDL block was determined by $^1$H-NMR as follows: a) the value of the integral of the PEG protons divided by 454 (average number of protons per one PEG 5000 chain) gave the integral value for one PEG proton and b) the number of HPMAmDL units in the polymers was determined from the ratio of the integral of the methine proton (CO—C H(CH$_3$)—OH) of HPMAmDL to the integral of one PEG proton. The number average molecular weight of the pHPMAmDL block was calculated from the resulting number of units.

Determination of the Critical Micelle Temperature (CMT) of the Different Block Copolymers The CMT of block polymer solution was determined with static light scattering using a Horiba Fluorolog fluorometer (650 nm, at a 90° angle). The polymers were dissolved at a concentration of 10 mg/mL in isotonic 120 mM ammonium acetate buffer (pH=5.0) at 0° C. The scattering intensity was measured every 0.2° C. during heating and cooling (the heating/cooling rate was approximately 1° C./min). Onsets on the X-axis, obtained by extrapolation of the intensity-temperature curves during heating to intensity zero were considered as the CMT. The CMT determinations were done at least two times and the deviations were smaller than 0.5° C.

Formation of Micelles

Micelles of block copolymers were formed by quickly heating an aqueous polymer solution from below to above CMT. The polymers were dissolved at a concentration of between 0.1 to 20 mg/mL in isotonic 120 mM ammonium acetate buffer (pH=5.0) at 0° C. in glass vials. Next, the polymer solution was quickly brought from 0° C. to 50° C. and was left at 50° C. for 1 minute. Before dynamic light scattering measurements, the micelle solution was incubated at 37° C.

Size Measurements of the Micelles

Dynamic light scattering (DLS) measurements were done to determine the size of the micelles, using Malvern 4700 system (United Kingdom) consisting of an Autosizer 4700 Spectrometer, a pump/filter unit, a Model 2013 air-cooler Argon ion laser (75 mW, 488 nm, equipped with a model 2500 remote interface controller, Uniphase) and a computer with DLS software (PCS, version 3.15, Malvern). The measurement temperature was 37° C. and the measurement angle was 90°. The change in solvent viscosity with temperature was corrected by the software.

Determination of the Critical Micelle Concentration (cmc)

The critical micelle concentration (cmc) of the different block copolymers was determined using pyrene as a fluorescence probe. Micelles of block copolymers were formed as described above in isotonic 120 mM ammonium acetate buffer (pH=5.0) at a concentration of 2 mg/mL. The micelle solutions with different polymer concentrations ranging from to 0.00001 mg/mL to 1.0 mg/ml were obtained by diluting the polymer solution with the same buffer at room temperature. Pyrene was dissolved in acetone at $1.8 \times 10^{-4}$ M and 15 µL of this solution was added to 4.5 mL of micelle solution, which gave $6.0 \times 10^{-7}$ M of pyrene in the mixture. The micelle solutions with pyrene were equilibrated at room temperature in the dark for 20 hours to allow the evaporation of acetone.

Fluorescence excitation spectra of pyrene were obtained using a Horiba Fluorolog fluorometer (at a 90° angle). The excitation spectra were recorded at 37° C. from 300 to 600 nm with the emission wavelength at 390 nm. The excitation and emission band slits were 4 nm and 2 nm, respectively. The intensity ratio of $I_{338}/I_{333}$ was plotted against polymer concentration to determine the CMC.

Micelle Destabilization

The destabilization of micelles was monitored at two different pHs (5.0 and 9.0). For pH 5.0, micelles of block copolymers were formed as described above in isotonic 120 mM ammonium acetate buffer (pH=5.0) at a concentration of 2 mg/mL. For pH 9.0, samples were prepared as follows. First, the polymers were dissolved in water at 20 mg/mL and then diluted 10-fold with 300 mM NaHCO₃ buffer (pH=9.0). Micelles were formed in the same way as described. For both samples, the size change of micelles and the change of scattering intensity in time were measured by dynamic light scattering at 37° C. The results are shown in FIG. 1. This figure shows that under conditions where hydrolysis of the lactic acid side groups is minimized (pH=5) the micelles were stable during the time of the measurements (60 hours). In contrast, at pH 9 a rapid destabilization of the micelles is observed.

This destabilization is due to hydrolysis of the lactic acid side groups. This hydrolysis is associated with an increase in hydrophilicity of the thermosensitive block. Once the hydrolysis has proceeded to such an extent that the LCST of this block passes 37° C., the micelles start to dissolve. This happens round 3-4 hours of incubation at 37° C. and pH 9.0. Since the hydrolysis of the lactic acid side groups is first order in hydroxyl ion concentration, a destabilization time of 120-160 hours at pH 7.4 can be expected.

Table 3 summarizes the characteristics of the different synthesised blockcopolymers.

EXAMPLE 4

Hydrogels Based on ABA Blockcopolymers of p(HPMAm-Dilactate) (A-Block) and PEG (b-Block)

Hydrogel forming ABA block copolymers of p(HPMAm-dilactate) (A-block) and PEG (b-block) were obtained using the same synthetic strategy as described for the synthesis of AB blockcopolymer (scheme 1). However, instead of the (PEG 5000)₂-ABCPA macroinitiator another type of macroinitiator was used. This initiator was synthesized by reaction of normal PEG (instead of monomethoxy PEG) with ABCAPA. In detail: 1 mmol of 4,4-azobis-(4-cyanopentanoic acid) (ABCPA), 3 mmol of N,N'-dicyclohexylcarbodiimide (DCC) and 0.3 mmol 4-(dimethyl-amino)pyridinium-4-toluenesulfonate (DPTS) were dissolved in mixture 1:1 of dry tetrahydrofuran (THF) and dichloromethane. The mixture was stirred at room temperature for 10 to 20 minutes. Next, 1 mmol poly(ethylene glycol) (PEG, number average molar mass 2000 or 4000) was added. This total mixture was stirred at room temperature for 20 h. Subsequently, the mixture was filtered and the solvent was evaporated. After evaporation, the product was dissolved in water en stirred for couple of hours and filtered to remove DCU. The filtrate was lyophilized to yield the PEG-ABCPA. ABA triblockcopolymers of p(HPMAm-dilactate) (A-block) and PEG (B-block) were obtained as described for the micelle forming AB block copolymers (p(HPMAm-dilactate)-b-PEG block copolymers).

The hydrogel forming properties of the different ABA blockcopolymers were studied using rheological analysis. In detail: 300 mg of polymer was dissolved in 700 µl of 100 mM ammomium acetate buffer pH 5 at 0° C. during 24 h. Next, 60 µl of this polymer solution applied to the rheometer (AR1000N, Ta instruments) equipped with a Cone/plate geometry with a radius of 1 cm and an angle of 1°. The temperature was gradually increased 0° C. to 50° C. at a ramp of 2° C./min. The rheological characteristics of the sample were monitored using a frequency of 1 Hz and a strain of 1%. For further experimental details: see De Jong S. J. et al. Novel self-assembled hydrogels by stereocomplex formation in aqueous solution of enantiomeric lactic acid oligomers grafted to dextran. Macromolecules 33, 3680-3686, 2000.

TABLE 3

Characteristics of pHPMAmDL-b-PEG block copolymers

| Polymers | $M_n$[a] | $M_w$[a] | $M_w/M_n$ | CMT (° C.)[b] | CMC (mg/mL)[c] | $Z_{ave}$ (nm)[d] |
|---|---|---|---|---|---|---|
| pHPMAmDL(3000)-b-PEG[e] | 7400 | 10400 | 1.41 | 12.5 | 0.15 | 60 ± 1 |
| pHPMAmDL(6900)-b-PEG[e] | 11900 | 23300 | 1.95 | 7.5 | 0.03 | 51 ± 1 |
| pHPMAmDL(13600)-b-PEG[e] | 15000 | 32800 | 2.18 | 6.0 | 0.015 | 53 ± 1 |

[a] $M_n$ = number average molar weight; $M_w$ = weight average molar weight determined by GPC
[b] Determined by SLS for 10 mg/mL solution in pH 5.0 buffer.
[c] Determined from pyrene excitation spectra at 37° C. in pH 5.0 buffer.
[d] Determined by DLS for 1 mg/mL solution in pH 5.0 buffer.
[e] Number in brackets is $M_n$ of HPMAmDL block determined by ¹H NMR. $M_n$ of PEG is 5000.

Table 4 summarizes the results.

TABLE 4

Rheological properties of ABA blockcopolymers (A = pHPMAmdilactate; B = PEG).

| Molecular weights (kDa) | | | | | |
|---|---|---|---|---|---|
| B block | A block | G' at 2° C. | G" at 2° C. | G' at 37° C. | G" at 37° C. |
| 4 | 11 | 6 | 40 | 830 | 1100 |
| 2 | 10 | 2 | 20 | 1600 | 2250 |

G' and G" in Pa · s

EXAMPLE 5

Fast degradable thermosensitive polymeric micelles based on PEG-block-poly(2-hydroxyethyl methacrylamide-lactate) were made based on the same methodology as described above.

Synthesis HEMAm-Oligolactates

The oligolactate esters of 2-hydroxyethyl methacrylamide (HEMAm-oligolactate) were obtained by ring-opening oligomerization of L-lactide, using HEMAm as the initiator and stannous octoate as a catalyst, essentially as described by Van Dijk et al. [Polymer 38 (1997), 6235-6242]. Briefly, L-lactide (33.5 g; 0.233 mol) and HEMAm (20 g; 0.155 mol) were stirred at 110° C. until the lactide was molten. 4-Methoxyphenol (~0.1 mol % relative to HEMAm) was added as radical scavenger. Subsequently, a catalytic amount of $SnOct_2$ (630 mg; 1 mol % with respect to HEMAm) was added. The resulting mixture was stirred for 2 hours and allowed to cool to room temperature. After dissolution of the product in 250 ml water-acetonitril (50:50), the HEMAm-oligolactate was fractionated with preparative chromatography essentially as described by Neradovic et al. [Macromolecules 36 (2003), 7491-7498]. The identity of HEMAm mono-, di, -tri-, and tetralactate (further abbreviated as HEMAm-$Lac_1$, HEMAm-$Lac_2$, HEMAm-$Lac_3$ and HEMAm-$Lac_4$) was confirmed by NMR; the purity by HPLC (system as described below).

Degradation Kinetics of HEMAm-Oligolactates

The degradation kinetic studies of HEMAm-oligolactates were conducted as described by Neradovic et al [Macromolecules; 2003; 36(20); 7491-7498]. In brief, a 10 mM solution of HEMAm-oligolactate in DMSO was diluted 10 times with 100 mM PBS (pH 7.4) in a glass vial and the pH was adjusted to pH 7.4 with 4 M HCl. The resulting solutions of HEMAm-monolactate, -dilactate, -trilactate and -tetralactate were incubated in a shaking water bath at 37° C. At regular time intervals samples of 300 μl were withdrawn and 700 μl of 1 M sodium acetate buffer (pH 3.8) was added to prevent further hydrolysis. The samples were stored at 4° C. prior to HPLC analysis. The hydrolysis of HEMAm-trilactate and -tetralactate was also investigated in an acetonitril-PBS pH7.2 mixture (50:50 w/w) of lower dielectric constant to slow down the hydrolysis rate. The HPLC analysis was carried out on a Waters system (Waters Associates Inc., Milford, Mass., USA). This consisted of a pump Model 600, an autoinjector Model 717, a variable wavelength absorbance detector Model 996 and an analytical reversed phase column LiChrosphere 100 RP-18 (5 μm, 125×4 mm i.d.) with an RP-18 guard column (4×4 mm) (Merck) was used. The injection volume was 50 μl and the detection wavelength was 254 nm. After 5 minutes isocratic flow of water/acetonitrile=95:5 (w/w), (eluent A), a gradient was run using eluent A and acetonitrile/water=95:5 (w/w), (eluent B). This gradient was run from 100% A to 100% B in 30 minutes with a flow rate of 1.0 ml/min. The chromatograms were analyzed with Empower Software Version 1154 (Waters Associates Inc.). Calibration curves were generated for each monomer and its degradation products with freshly prepared standard solutions in DMSO/PBS pH 7.2 (100 mM)/sodium acetate buffer pH 3.8 (1 M) (3:27:70) and were at least linear between 0.07 and 15 μM.

Results showed that monodisperse HEMAm-oligolactates hydrolyzed to the unsubstituted HEMAm and lactic acid when incubated in pH 7.4 at 37° C. The overall mass balance showed that the amide bond in HEMAm(lactates) was stable under the selected conditions. Concentrations of HEMAm-$Lac_1$ to HEMAm-$Lac_4$ were determined by the HPLC method described above. From the concentration versus time plots, the half-lives (t½) were determined. Stock solutions in DMSO were diluted ten times in PBS buffer to solubilize the oligolactates. Therefore, the reported half life times are expected to be about twice as high in 100% water, as discussed by Neradovic et al. [Macromolecules 36 (2003), 7491-7498].

The half life times of the prepared HEMAm-$Lac_1$ and HEMAm-$Lac_2$ are 58 and 5.6 hours respectively. At similar conditions (pH 7.5, 10% DMSO) the half life of the methacrylate analogue of the HEMAm-lactates i.e. N-(2-hydroxyethyl)methacrylate (HEMA) mono- and dilactate were 31 hours and 3 hours respectively (Neradovic et al, Macromolecules 36 (2003), 7491-7498)

The half life times of HPMAm-monolactate and HPMAm-dilactate are respectively 87.5 and 15.4 hours. Thus, the HEMAm-lactate offers the possibility to provide micelles with a shorter half-life than the analogous HPMAm-lactate, but a higher half-life than the analogous HEMA-lactate. Thereby it is anticipated that the degradation profile of the corresponding (co)polymers can be fine-tuned to become suitable as a delivery system for an active compound.

HEMAm derivatives with three and four lactic acid units (HEMAm-$Lac_3$ and HEMAm-$Lac_4$) display even faster hydrolysis kinetics than HEMAm-$Lac_{1-2}$. In order to compare our results with the half life times obtained for the previously reported HPMAm-oligolactates with 7 and 12 lactate units [Van Nostrum et al, Polymer 45 (2004), 6779-6787], we carried out the degradation experiments in 50% ACN—PBS 7.2 as well. The half lives of HPMAm oligolactates (7 and 12 lactate units) under these conditions were 3.1 hours, which is only slightly shorter than those of HEMAm-Lac3 and HEMAm-Lac4. Thus, an increasing lactate chain length increases the hydrolysis rates of oligolactates until it levels off between 4 and 7 lactate units per oligolactate chain. It is envisaged that the higher lactates (in particular the trilactate and the tetralactate polymer) are in particular useful to be used in a blend or copolymer with another polymer according to the invention, in order to modify the half time and the stability of a delivery system comprising such blend.

Synthesis of (Co)-Polymers of HEMAm-Oligolactates

The (co)polymers were synthesized via free radical polymerization in airtight screw-cap glass vials. AIBN dissolved in 1,4-dioxane (ratio of monomers/initiator=100:1 and 150:1 mol/mol) was added to a 200 mg/ml monomer solution (total volume approximately 1 ml dioxane) Both homopolymers (HEMAm, HEMAm-Lac$_n$) and copolymers (made from mixtures of HEMAm-Lac$_2$ and HEMAm-Lac$_4$) were synthesized.

A nitrogen flow was led through the solution for at least 10 minutes. The polymerization was conducted at 70° C. for 24 hours while stirring the solution. Next, the polymers were precipitated by dropwise addition of the solution to an excess of diethyl ether. After centrifugation, the residue was dried overnight in a vacuum oven at 40° C. $^1$H-NMR (DMSO, d$_6$): δ=7.5 (b, CO—NH—CH$_2$), 5.5 (b, CH—OH), 5.0 (b, CO—CH(CH3)-O), 4.1 (b, CO—CH—(CH3)-OH), 4.0 (b, CH2-CH2-O), 1.4, (b, CO—CH—CH3), 1.3 (b, HO—CH—CH3), 1.0-0.6 (polymer main chain protons).

The HEMAm-Lac$_2$/HEMAm-Lac$_4$ comonomer ratio (mol/mol) in the copolymer was determined by $^1$H NMR from the ratio of the integral of the methyn protons (δ=5.0 ppm) to the alcoholic proton (δ=5.5 ppm). The following equation was used:

$$\% \ HEMAm\text{-}Lac_4 = (I_{5.0} - I_{5.5})/2 * 100\% \quad (1)$$

For GPC analysis of the molecular weights and their distribution of the different polymers, a Plgel 3 μm MIXED-D column (Polymer Laboratories) was utilized at a Waters System (Waters Associates Inc., Milford, Mass., USA) with a differential refractometer Model 410. Poly(ethyleneglycol) of defined molecular weights were used as standards. The eluent was DMF containing 10 mM LiCl. The samples were dissolved overnight at a concentration of 5 mg/ml in the eluent and prior to analysis filtered through a 0.45 μm filter. The elution rate was 0.7 ml/min and the temperature was 40° C. Aqueous GPC was performed on the same system with 5 mM ammonium acetate buffer (pH 5.5), PL 8 μm aquagel OH column (Polymer Laboratories) and dextran standards. Peak areas were determined with Empower Software Version 1154 (Waters Associates Inc).

The following Table 5 summarizes the results of all homopolymerizations.

TABLE 5

Characteristics of the homopolymers of HEMAm-oligolactates

| Monomer | Ratio [M]/[I] | Yield (%) | M$_w$ (GPC) | M$_w$/M$_n$ | CP (° C.) |
|---|---|---|---|---|---|
| HEMAm | 150:1 | 92 | 24000$^a$ | 3.7 | >75 |
| HEMAm-Lac$_1$ | 150:1 | 71 | 53000 | 3.1 | >75 |
| HEMAm-Lac$_2$ | 100:1 | 81 | 68000 | 3.0 | 21.7 |
| HEMAm-Lac$_3$ | 75:1$^b$ | 83 | 24000 | 3.3 | <0 |
| HEMAm-Lac$_4$ | 100:1 | 76 | 57700 | 3.0 | <0 |

$^a$Insoluble fraction present
$^b$Twice as much AIBN added because the DP3 monomer contained still some radical scavenger hydroquinone after purification (preparative HPLC)

HEMAm was almost quantitatively converted. The DMF solution for GPC analysis however was slightly cloudy and the filtration through 0.45 μm filter was difficult. The product did however fully dissolve in water and was therefore analyzed by aqueous GPC. This analysis gave a monomodal distribution with an average molecular weight of 194000 g/mol and a polydispersity of 22. The pHEMAm-oligolactates were obtained in a constant high yield (around 80%).

The thermosensitive properties of the polymers were investigated by static light scattering. To prevent hydrolysis, a pH 5 buffer was used. pHEMAm-Lac$_3$ and pHEMAm-Lac$_4$ did not dissolve after overnight incubation at 0°, suggesting a cloud point below 0° C.

The homopolymers of HEMAm and its monolactate derivative did not show any scattering up to 75° C. The homopolymer of pHEMAm-Lac$_2$ displayed its CP at 21.7° C.

The copolymers of HEMAm-Lac$_2$ and HEMAm-Lac$_4$ were synthesized with monomer to AIBN ratio of 100:1. Table 6 summarizes their characteristics.

Figure 7:
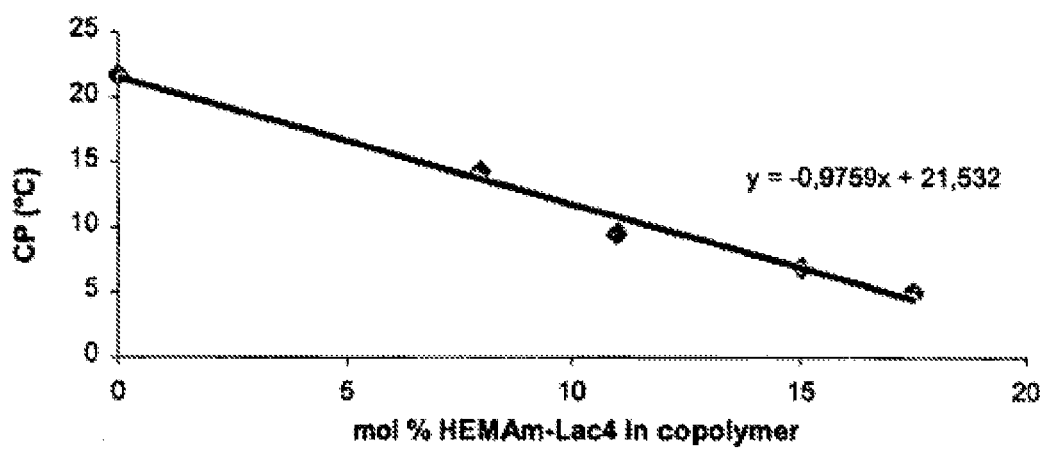
FIG. 7 shows the CP of a copolymer of the invention (pHEMAm-lactate) as a function of the tetralactate content in the polymer

The yields and molecular weights were comparable with the homopolymers. The copolymer composition corresponds with the feed ratio. The CP behavior of these copolymers (FIG. 7) showed that the amount of hydrophobic HEMAm-Lac4 incorporated linearly influenced the CP. From this curve, it was predicted that a copolymer with 22% HEMAm-Lac$_4$ or more would not dissolve at 0°. This was experimentally confirmed (Table 6).

TABLE 6

Characteristics of copolymers HEMAm-Lac$_2$/HEMAm-Lac$_4$

| HEMAm-Lac$_2$/ HEMAm-Lac$_4$ feed ratio | Yield (%) | % HEMAm-Lac$_4$ incorporated$^a$ | M$_w$ (GPC) | M$_w$/M$_n$ | CP (° C.) |
|---|---|---|---|---|---|
| 94%-6% | 79 | 8 | 71000 | 3.0 etc | 14.3 |
| 88%-12% | 76 | 11 | 62280 | 2.85 | 9.5 |
| 85%-15% | 88 | 15 | 69000 | 2.48 | 6.9 |
| 82%-18% | 77 | 18 | 68310 | 2.98 | 5 |
| 76%-24% | 76 | 23 | 60820 | 2.76 | <0 |

$^a$The amount of DP4 incorporated in the polymer chain is derived from $^1$H NMR.

Block Copolymers of PEG and HEMAm-Oligolactates

Block copolymers with HEMAm-Lac$_n$ as thermosensitive block and PEG as hydrophilic block were prepared via the macroinitiator route as described by Neradovic et al. [Macromolecules, 2001, 34; 7589-7591]. Poly(ethyleneglycol) (PEG)$_{5000}$ was chosen to be the hydrophilic part of the block-copolymer as this polymer favor longer circulation time of nanoparticles drug carriers and lower uptake by the RES.

In brief, block copolymers were prepared by radical polymerization using PEG$_2$-ABCPA as initiator (ratio of monomer/initiator=150:1 mol/mol). The concentration of starting material was 300 mg/ml in acetonitrile in airtight glass vials. A nitrogen flow was led through the solution for at least 10 minutes.

The polymerization was conducted at 70° C. for 24 hours. Next, by dropwise addition of the solution to an excess of diethyl ether, the polymers were precipitated. After centrifugation, the residue was dried overnight in a vacuum oven at 40° C.

$^1$H-NMR (DMSO, d$_6$) (see FIG. 2): δ=7.5 (b, CO—NH—CH2), 5.5 (b, CH—OH), 5.0 (b, CO—CH(CH3)-O), 4.1 (b, CO—CH—(CH3)-OH), 4.0 (b, CH2-CH2-O), 3.6 (b, PEG methylene protons, O—CH2-CH2), 1.4, (b, CO—CH—CH3), 1.3 (b, HO—CH—CH3), 1.0-0.6 (pHEMAm-Lac$_n$ main chain protons).

The number average molecular weight (M$_n$) of the thermosensitive block was determined by $^1$H-NMR as follows (in the situation of copolymers, an average molecular weight of the monomers M was used):

$$M_n = M_{ave}(HEMAm\text{-}Lac_n) \times I_{HEMAm\text{-}Lacn}/(I_{PEG}/454) \quad (2)$$

I$_{HEMAm\text{-}Lacn}$ is the value of the integral of the hydroxyl proton of the HEMAm-Lac$_n$ (H$_{oh}$ δ=5.5 ppm); I$_{PEG}$ is the value of the integral of the PEG protons and is divided by the average number of protons per one PEG$_{5000}$ chain (=454).

A block copolymer of PEG and HEMAm-Lac$_2$ as well as block copolymers with twenty percent HEMAm-Lac$_4$ and eighty percent HEMAm-Lac$_2$ with varying monomer to initiator ratios were synthesized. The latter polymers contained HEMAm-Lac$_4$ to obtain a polymer with a CP just above 0° C. Table 7 summarizes the characteristics of the obtained block-copolymers.

the concentration range 0.5-10 mg/ml, the particle size were relatively small (70 nm) with a low polydispersity. 2 mg/ml polymer solutions were used for further measurements as this gave the lowest PD.

TABLE 7

Characteristics of block copolymers PEG-b-(HEMAm-oligolactate)

| Block copolymer | Ratio monomer:initiator | % HEMAm-Lac$_4$ incorporated[a] | Yield (%) | M$_w$ (GPC) | M$_w$/M$_n$ | M$_n$ HEMAm block (NMR) | CMT (° C.)[b] | CMC (mg/L) | Micelle size (ZAve)[b] | Micelle PD[b] |
|---|---|---|---|---|---|---|---|---|---|---|
| PEG-HEMAm-Lac$_2$ | 150:1 | — | 69 | 49000 etc | 2.3 etc | 9800 | 20 | n.d.[c] | 124 | 0.1 |
| PEG-(HEMAm-Lac$_2$/HEMAm-Lac$_{4)}$ | 150:1 | 21 | 85 | 35870 | 3.1 | 10600 | 5.9 | 0.08 | 70 | 0.08 |
| PEG-(HEMAm-Lac$_2$/HEMAm-Lac$_{4)}$ | 100:1 | 20 | 95 | 50000 | 2.1 | 25100 | | | 78 | 0.2 |
| PEG-(HEMAm-Lac$_2$/HEMAm-Lac$_{4)}$ | 50:1 | 20 | 82 | 30100 | 1.9 | 12000 | | | 68 | 0.1 |

[a]The amount of HEMAm-Lac$_4$ incorporated in the polymer chain is derived from $^1$H NMR.
[b]2 mg/ml solution $^1$H NMR was used to calculate the number average molecular weights of the thermosensitive block. These were significant lower than the GPC results.

However, the GPC was calibrated with narrow poly(ethyleneglycol) standards and the M$_n$ is therefore not the absolute molecular weight of the polymer. The block copolymer PEG-b-(80% HEMAm-Lace-20% HEMAm-Lac$_4$) has a cloud point of 5.9° C., which is slightly higher than CP of the copolymer of 82% HEMAm-Lac$_2$-18% HEMAm-Lac$_4$ (table 6, 5.0° C.). From this result it is concluded that a PEG block slightly increases the CP.

Formation and Characterization of PEG-HEMAm-Lac$_n$ Micelles

Micelles were formed via the quick heating procedure of aqueous polymer solutions as described in example 3. The particle size and particle size distributions are displayed in Table 7. The incorporation of 20% HEMAm-Lac$_4$ in the thermosensitive block caused a significant decrease in particle size. This is found to be relatively independent of the length of the thermosensitive block. The presence of longer hydrophobic lactate side chains increases the hydrophobic interactions and creates a more compact micellar core.

Figure 8:
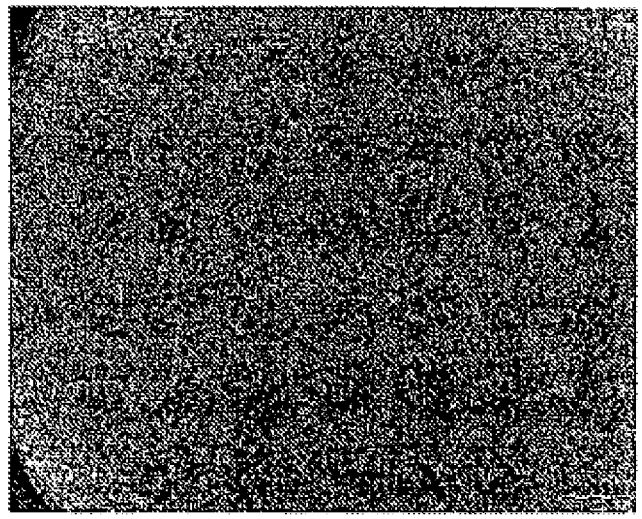
FIG. 8 shows a CryoTEM picture of a micellar solution of a polymer according to the invention.

The morphology of the micelle was studied with CryoTEM. FIG. 8 shows a representative microphotograph and shows the spherical shape of the micelles as well as their narrow particle size distribution.

Figure 9:
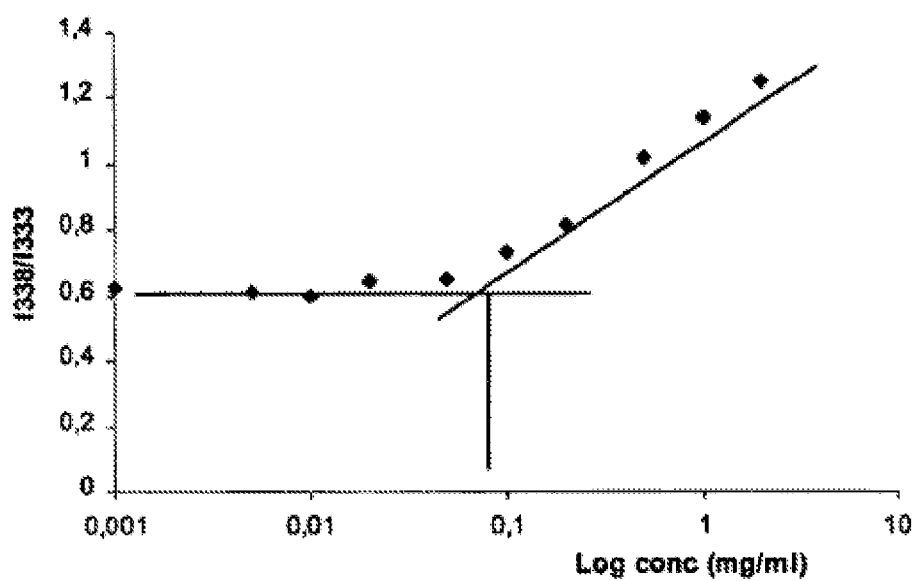
FIG. 9 shows a plot for determining the cmc of a polymer according to the invention.
Figure 10:
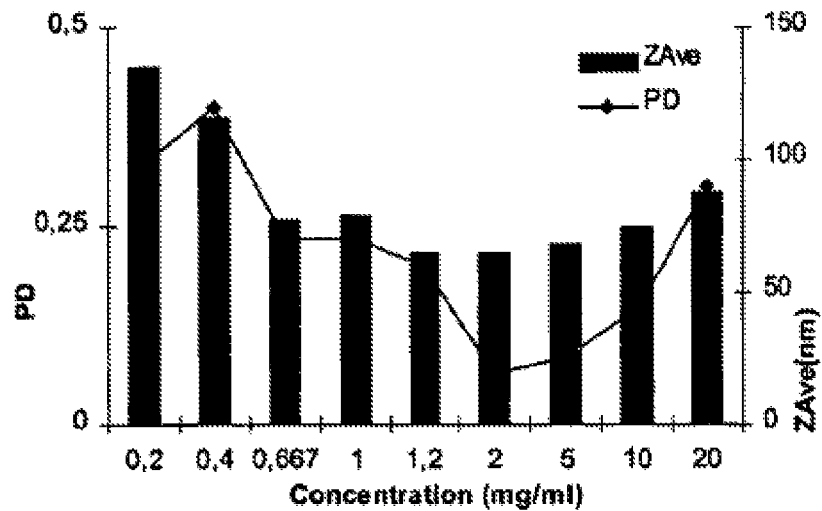
FIG. 10 shows the effect of the concentration of a polymer according to the invention on the particle size of the micelles.

The critical micelle concentration (cmc) was determined with pyrene as a fluorescent probe [see example 3]. The cmc was determined from the plot of the intensity ratio $I_{338}/I_{333}$ as a function of the concentration of block copolymer (FIG. 9). For the block copolymer PEG-b-(80% HEMA-Lac$_2$-20% HEMAm-Lac$_4$), the cmc was determined to be 0.08 mg/ml, which is low enough for systemic administration in vivo. The particle sizes of micelles prepared from polymer solutions at various concentrations above the cmc (0.2-20 mg/ml) are shown in FIG. 10.

Figure 11:
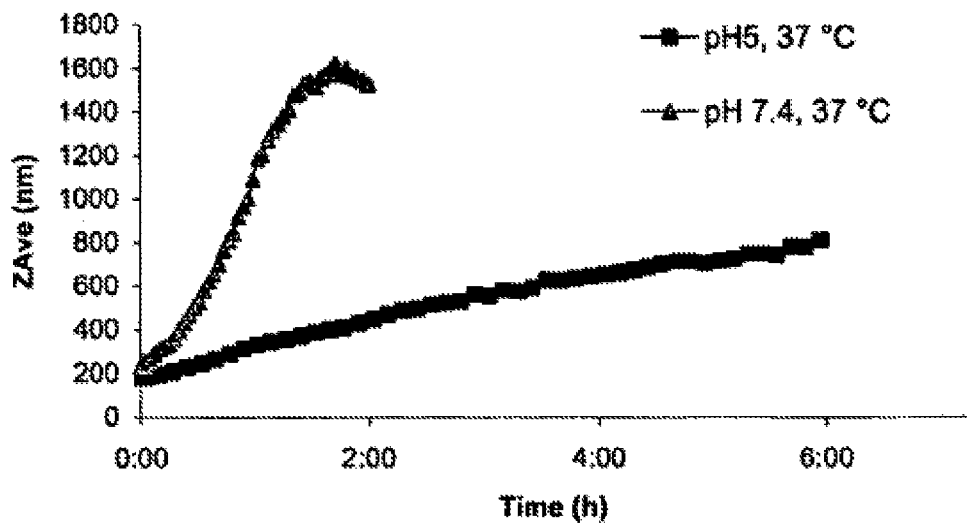
FIG. 11 shows the particle size stability of PEG-b-p(HEMAm-dilactate) versus time

Relative large and polydisperse micelles are formed at concentrations below 0.5 mg/ml which is close to the cmc. In pH Dependent Stability of the Micelles The PEG-b-pHPMAm-dilactate micelles (see example 3) dissolved after approximately one week incubation at physiological conditions (aqueous buffer pH 7.4, 37° C.). The stability of the micelles of PEG-b-pHEMAm-lac$_2$ was followed by DLS measurements during incubation in buffer pH 5 at 37° C. to slow down hydrolysis. Under these conditions, the micellar particle size gradually increased in time (FIG. 11).

Figure 12:
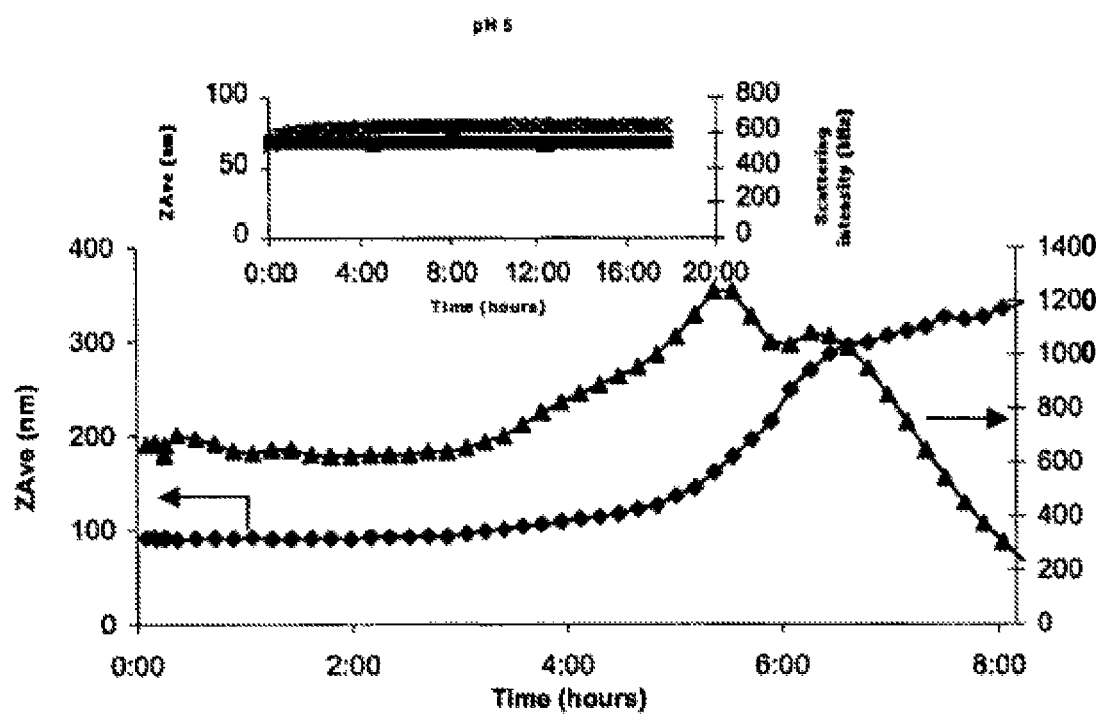
FIG. 12 shows the particle size stability of another polymer according to the invention

As opposed to PEG-b-HEMAm-Lac$_2$, incorporation of 20% HEMAm-Lac$_4$ increased the hydrophobicity of the thermosensitive block which resulted not only a smaller particle size (Table 7) but also a higher stability of the micelles at pH 5 (FIG. 12). For PEG-b-(80% HEMAm-Lac$_2$-20% HEMAm-Lac$_4$) at pH 5, a constant particle size was observed for at least 18 hours. At pH 7.4 and 37° C., the particle size hardly changed during the first three hours, followed by a swelling phase until 8 hours. After that period, the micelles started to dissolve as seen by the measured scattering intensity which dropped to zero.

CONCLUSION

Thermosensitive (block co) polymers of HEMAm-oligolactates were synthesized in high yields by free radical polymerization. It is possible to accurately tailor the cloud point by adjusting the copolymer composition of the poly(HEMAm-oligolactates). The increase in hydrophobicity of the thermosensitive block (poly(HEMAm-Lac$_2$)) influenced not only the CP but also the micellar particle size and stability. Twenty percent of HEMAm-Lac$_4$ was sufficient to increase the hydrophobicity sufficiently to produce highly stable micelles. An important issue determining the effectiveness of a micellar drug carrier is the ability to control the time over which drug release takes place, which can be done by a (micellar) drug release system according to the invention This is advantageous over nondegradable micellar systems as described in the prior art (e.g. PEG-poly(glutamic acid) [Kataoka J Contr Release 2005, p 223]. Herein drug release is only mediated by diffusion, which is a slow process and difficult to control. The thermosensitive polymeric micelles described here have the advantage over nondegradable micelles or liposomes by their ability to destabilize after an induction period that can be tailored by selecting the building block of the polymer quantitatively and/or qualitatively. For instance the HEMAm-lactate polymer is capable of providing a micellar system that is stable for approximately 3 hours and thereby controlling the release of encapsulated drugs. Furthermore the degradation products are expected to be bioresorbable, i.e. degradable with elimination from the human body. After destabilization of the micelles, it is contemplated that the remaining polymers (Mw<50000) will usually not exhibit toxicity caused by long-term accumulation because it will be excreted by glomerular filtration [Delgado C, Francis G E, Fisher D 1992, The uses and properties of PEG-linked proteins. Crit Rev Ther Carrier Syst 9: 249-304]. The unique profile of micelle destabilization may be advantageous for in vivo use because the observed induction period is just long enough to allow accumulation of the micelles at the site of e.g. a tumor.

The invention claimed is:

1. A temperature sensitive polymer having a lower critical solution temperature that changes during incubation in an aqueous solution or medium, which polymer is a homopolymer of a hydrophobically modified hydroxyalkylmethacrylamide or an interpolymer of a hydrophobically modified hydroxyalkylmethacrylamide and comonomers selected from N-vinyl-pyrrolidone, vinyllactates and vinylethers wherein said comonomers are included in the interpolymer at a mole % less than and not including 50 mole %.

2. The polymer of claim 1, wherein the polymer comprises a hydrophobic group which is bound to the hydroxyl group of the hydroxyalkylmethacrylamide by a hydrolysable bond.

3. The polymer of claim 2, wherein the hydrophobic group is lactic acid or lactic acid oligomer.

4. The polymer of claim 2, wherein the hydrolyzable bond is selected from esters, orthoesters, amides, carbonates, carbamates, anhydrides, ketals, and acetals.

5. The polymer of claim 1, which polymer is a homo or interpolymer of N-2-hydroxyalkylmethacrylamide lactate.

6. The polymer of claim 5, which polymer is a homopolymer of N-2-hydroxyethylmethacrylamide lactates or N-2-hydroxypropylmethacrylamide lactates.

7. The polymer of claim 1, wherein the polymer comprises at least one component selected from monolactates, dilactates, trilactates and tetralactates.

8. The polymer of claim 1, having a lower critical solution temperature before incubation below human body temperature and a different lower critical solution temperature after incubation above human body temperature.

9. A controlled release system comprising the temperature sensitive polymer of claim 8 and an active ingredient.

10. The controlled release system of claim 9, wherein the polymer is in the form of a polymeric micelle in which a hydrophilic block is present which hydrophilic block comprises a polyalkyleneglycol.

11. The controlled release system of claim 10, wherein the hydrophilic block comprises polyethyleneglycol.

12. The polymer of claim 1, which is a homopolymer of said hydrophobically modified hydroxyalkyl(meth)acrylamide.

13. A controlled release system comprising the temperature sensitive polymer of claim 12 and an active ingredient.

14. A targeting drug composition, comprising a drug and particles of the controlled release system of claim 13.

15. The temperature sensitive polymer of claim 1 which is an interpolymer of a hydrophobically modified hydroxyalkylmethacrylamide and comonomers selected from N-vinyl-pyrrolidone, vinyllactates and vinylethers wherein said comonomers are included in the interpolymer at a mole % less than and not including 50 mole %.

16. A controlled release system comprising a temperature sensitive polymer and an active ingredient, wherein the system is in the form of a hydrogel,
wherein the temperature sensitive polymer has a lower critical solution temperature that changes during incubation in an aqueous solution or medium, which polymer is a homopolymer of a hydrophobically modified hydroxyalkylmethacrylamide or an interpolymer of a hydrophobically modified hydroxyalkylmethacrylamide and comonomers selected from acrylates, methacrylates, methacrylamides, N-vinyl-pyrrolidone, vinyllactates and vinylethers wherein said comonomers are included in the interpolymer at a mole % less than and not including 50 mole %.

17. The controlled release system of claim 16, wherein the hydrogel is an ABA block copolymer, wherein block A is a temperature sensitive polymer of claim 1 and B is a hydrophilic polymer.

18. The controlled release system of claim 17, wherein B is polyalkyleneglycol.

19. The controlled release system of claim 18, wherein B is polyethyleneglycol.

20. A targeting drug composition, comprising a drug and particles of the controlled release system of claim 9.

21. The targeting drug composition of claim 20, which further comprises a homing device.

22. The targeting drug composition of claim 20, wherein the particles have an average diameter of less than 200 nm.

23. The targeting drug composition of claim 22, wherein the particles have an average diameter in the range of 10 to 100 nm.

* * * * *